(12) United States Patent
Hirata

(10) Patent No.: US 11,635,364 B2
(45) Date of Patent: Apr. 25, 2023

(54) OBSERVATION DEVICE

(71) Applicant: Evident Corporation, Nagano (JP)

(72) Inventor: Tadashi Hirata, Tokyo (JP)

(73) Assignee: EVIDENT CORPORATION, Nagano (JP)

( * ) Notice: Subject to any disclaimer, the term of this patent is extended or adjusted under 35 U.S.C. 154(b) by 223 days.

(21) Appl. No.: 17/101,581

(22) Filed: Nov. 23, 2020

(65) Prior Publication Data

US 2021/0102887 A1 Apr. 8, 2021

Related U.S. Application Data

(63) Continuation of application No. PCT/JP2019/022520, filed on Jun. 6, 2019.

(30) Foreign Application Priority Data

Jun. 8, 2018 (WO) .................. PCT/JP2018/022027

(51) Int. Cl.
*G06K 9/00* (2022.01)
*G01N 15/14* (2006.01)
(Continued)

(52) U.S. Cl.
CPC ....... *G01N 15/1475* (2013.01); *G02B 21/365* (2013.01); *G06T 7/0016* (2013.01);
(Continued)

(58) Field of Classification Search
CPC ....... G06T 2207/30242; G06T 7/70–77; G06T 7/97; G06T 2207/10056–10061;
(Continued)

(56) References Cited

U.S. PATENT DOCUMENTS

2002/0071121 A1* 6/2002 Ortyn .................. G02B 27/145
356/417
2002/0177885 A1 11/2002 Eisfeld et al.
(Continued)

FOREIGN PATENT DOCUMENTS

EP 2 490 008 A2 8/2012
EP 2 749 226 A1 7/2014
(Continued)

OTHER PUBLICATIONS

International Search Report dated Aug. 21, 2018 received in PCT/JP2018/022027.
(Continued)

*Primary Examiner* — Atiba O Fitzpatrick
(74) *Attorney, Agent, or Firm* — Scully, Scott, Murphy & Presser, P.C.

(57) ABSTRACT

Provided is an observation device including: a stereo image-acquisition optical system that acquires images of cells floating in a culture fluid inside a culture vessel; and an analyzer that calculates a cell density of the cells on the basis of the images acquired by the stereo image-acquisition optical system, wherein the analyzer identifies a three-dimensional position of each of the cells included in the images and calculates the cell density on the basis of the number of cells present within a predetermined three-dimensional region.

18 Claims, 35 Drawing Sheets

(51) Int. Cl.
*G02B 21/36* (2006.01)
*G06T 7/00* (2017.01)

(52) U.S. Cl.
CPC ............... *G06T 2207/10056* (2013.01); *G06T 2207/30024* (2013.01)

(58) Field of Classification Search
CPC ......... G06T 2207/30024; C12M 41/36; C12M 1/34; C12M 27/00–02; C12M 21/00–18; C12M 23/14; C12M 31/00–12; G01N 2015/1486; G01N 15/02; G01N 15/06–2015/0693; G01N 15/1475; G06V 2201/12–122; G06V 30/19013; G06V 20/69–698; G06V 2201/04; C12N 2513/00; G02B 21/365–367
See application file for complete search history.

(56) References Cited

U.S. PATENT DOCUMENTS

| | | | |
|---|---|---|---|
| 2005/0047640 | A1 | 3/2005 | Eisfeld et al. |
| 2005/0185050 | A1 | 8/2005 | Ohashi |
| 2006/0251314 | A1 | 11/2006 | Eisfeld et al. |
| 2007/0146873 | A1* | 6/2007 | Ortyn .............. G02B 27/0075 359/386 |
| 2009/0191619 | A1 | 7/2009 | Eisfeld et al. |
| 2010/0208046 | A1 | 8/2010 | Takahashi |
| 2011/0254948 | A1 | 10/2011 | Eisfeld et al. |
| 2011/0318725 | A1* | 12/2011 | Suenaga ............. C12M 41/40 435/372.3 |
| 2012/0114219 | A1 | 5/2012 | Nakagawa et al. |
| 2012/0214250 | A1 | 8/2012 | Oura et al. |
| 2014/0187902 | A1 | 7/2014 | Sato et al. |
| 2014/0240314 | A1* | 8/2014 | Fukazawa ............ G06T 15/00 345/419 |
| 2016/0331243 | A1 | 11/2016 | Irisawa et al. |
| 2017/0254784 | A1 | 9/2017 | Murayama |
| 2018/0140199 | A1 | 5/2018 | Sangu |
| 2019/0070608 | A1 | 3/2019 | Kikuchi et al. |
| 2019/0212537 | A1 | 7/2019 | Ohashi et al. |
| 2019/0220979 | A1 | 7/2019 | Aoki et al. |
| 2019/0333215 | A1* | 10/2019 | Ariga .................... C12M 1/00 |
| 2020/0239827 | A1 | 7/2020 | Sasaki et al. |
| 2021/0027043 | A1* | 1/2021 | Dohi ................. G02B 23/2469 |
| 2021/0102887 | A1 | 4/2021 | Hirata |

FOREIGN PATENT DOCUMENTS

| | | |
|---|---|---|
| EP | 3 100 684 A1 | 12/2016 |
| EP | 3 287 080 A1 | 2/2018 |
| EP | 3 454 042 A1 | 3/2019 |
| EP | 3 470 510 A1 | 4/2019 |
| EP | 3 473 998 A1 | 4/2019 |
| JP | 2004-512845 A | 4/2004 |
| JP | 2005-241791 A | 9/2005 |
| JP | 2008-263990 A | 11/2008 |
| JP | 2009-022295 A | 2/2009 |
| JP | 2010-128354 A | 6/2010 |
| JP | 2011-206066 A | 10/2011 |
| JP | 2011-247965 A | 12/2011 |
| JP | 2012-170357 A | 9/2012 |
| JP | 2013-113804 A | 6/2013 |
| JP | 2014-126400 A | 7/2014 |
| JP | 2014-128320 A | 7/2014 |
| JP | 2015-139507 A | 8/2015 |
| JP | 2016-202631 A | 12/2016 |
| JP | 2017046620 A * | 3/2017 |
| JP | 2017-140006 A | 8/2017 |
| JP | 2017-140007 A | 8/2017 |
| JP | 2019-041724 A | 3/2019 |
| JP | 2019-179061 A | 10/2019 |
| JP | 2020-122686 A | 8/2020 |
| JP | 2020-174574 A | 10/2020 |
| WO | 2002/037938 A2 | 5/2002 |
| WO | WO-2005056813 A3 * | 8/2006 .......... B01F 13/0059 |
| WO | 2011/010449 A1 | 1/2011 |
| WO | 2015/114919 A1 | 8/2015 |
| WO | 2016/084217 A1 | 6/2016 |
| WO | 2017/217148 A1 | 12/2017 |
| WO | 2017/217180 A1 | 12/2017 |
| WO | WO-2018154871 A1 * | 8/2018 |
| WO | 2019/188765 A1 | 10/2019 |
| WO | 2019/234916 A1 | 12/2019 |
| WO | 2019/235563 A1 | 12/2019 |

OTHER PUBLICATIONS

International Search Report dated Jul. 9, 2019 received in PCT/JP2019/022520.
Hirose, S. et al.,"Immortalization of Erythroblasts by c-MYC and BCL-XL Enables Large-Scale Erythrocyte Production from Human Pluripotent Stem Cells", Stem Cell Reports, vol. 1, Issue 6,pp. 499-508,pp. 501-503; Dec. 17, 2013.
Strohm, E. M. et al.,"Probing Red Blood Cell Morphology Using High-Frequency Photoacoustics", Biophysical Journal,vol. 105, pp. 59-67 pp. 59-60, 65; 2013.
Gnyawali V. et al.,"Simultaneous acoustic and photoacoustic microfluidic flow cytometry for label-free analysis", Scientific Reports,9:1585, pp. 1-11 Abstract, pp. 4-5; Feb. 7, 2019.
Saha R. K. et al.,"Computational Investigation on the Photoacoustics of Malaria Infected Red Blood Cells", PLOSONE, vol. 7,Issue 12, e51774,pp. 1-9,Abstract, pp. 1-2; Dec. 14, 2012.
"Tabulated Molar Extinction Coefficient for Hemoglobin in Water", Retrieved from the Internet, URL:https://omlc.org/spectra/hemoglobin/summary.html; retrieved from the Internet in Sep. 2019.
International,Search Report dated Apr. 7, 2020 received in PCT/JP2020/001798.

* cited by examiner

FIG. 24
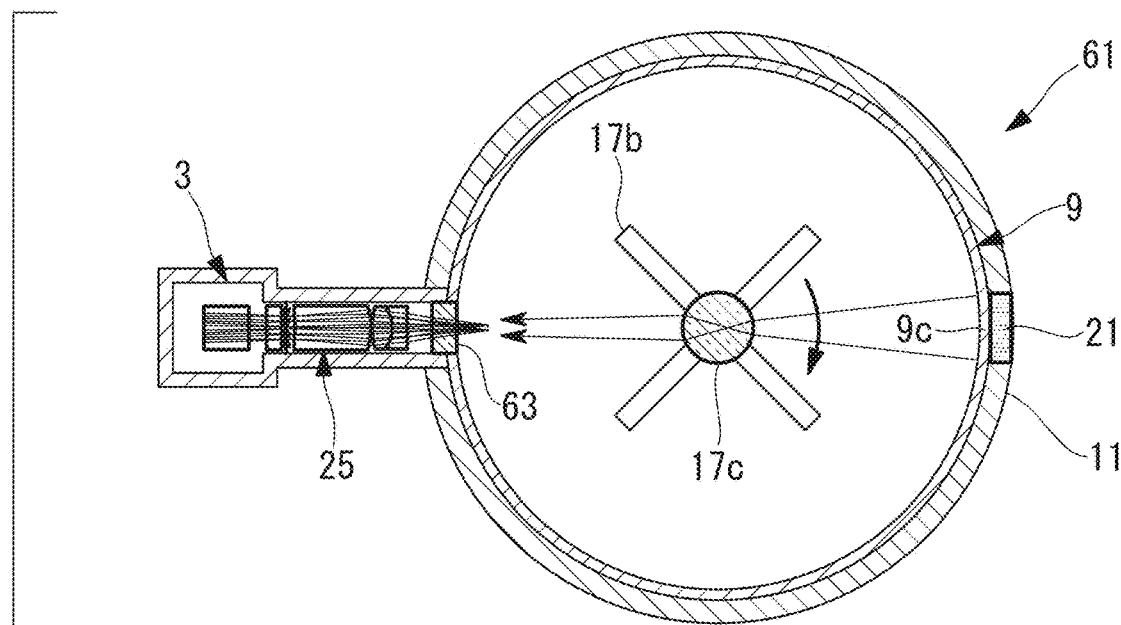
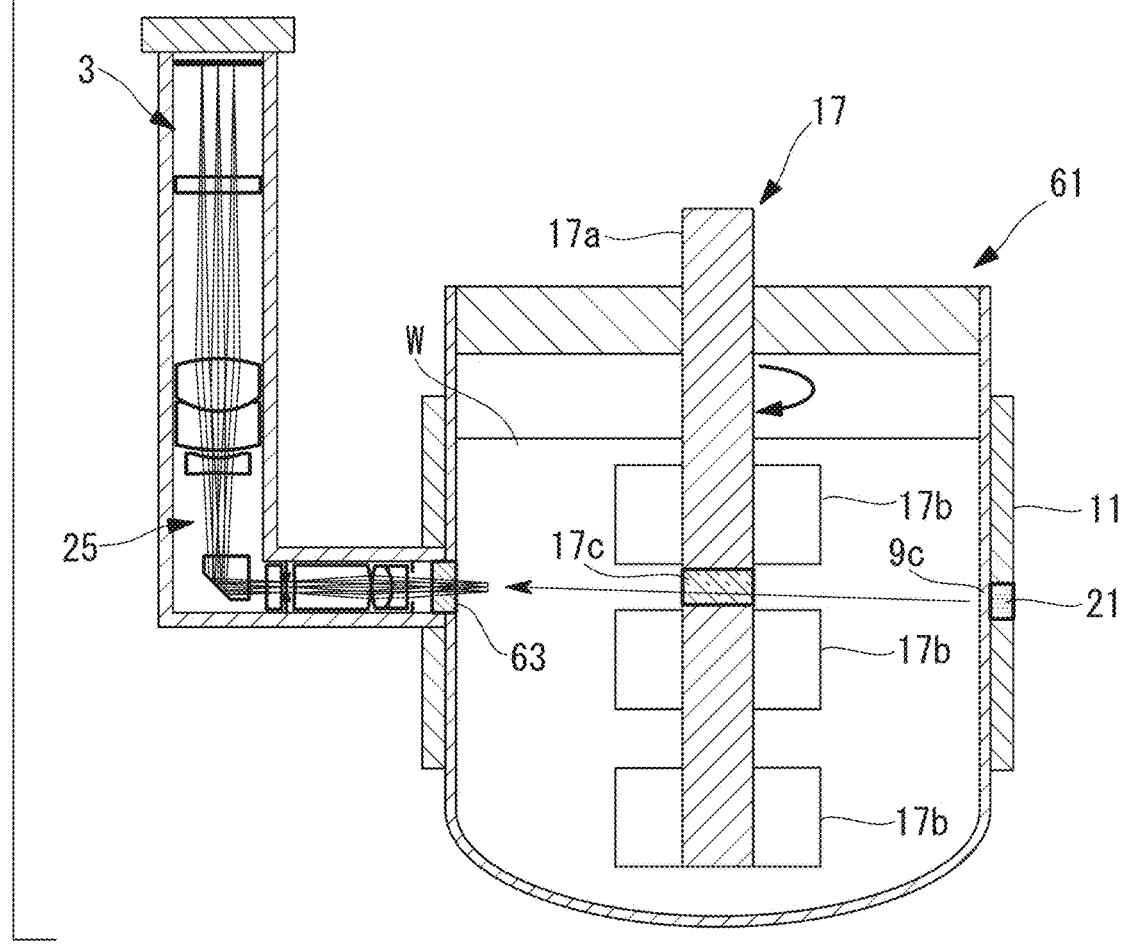

OBSERVATION DEVICE

CROSS-REFERENCE TO RELATED APPLICATIONS

This is a continuation of International Application PCT/JP2019/022520 which is hereby incorporated by reference herein in its entirety.

This application claims the benefit of International Application PCT/JP2018/022027, the content of which is incorporated herein by reference.

TECHNICAL FIELD

The present invention relates to an observation device.

BACKGROUND ART

In recent years, in the field of regenerative medicine, including the field of iPS cells (induced pluripotent stem cells), scaling-up of cell culturing has been desired. For the mass production of cells, the culturing is changing from conventional adherent culturing using a vessel called a well plate or dish to suspension culturing using a suspension culture vessel called a bioreactor. In suspension culturing using a suspension culture vessel, cells are cultured in a state in which the cells are made to float in a liquid by stirring the liquid inside the suspension culture vessel.

As a method for observing cells using a suspension culture vessel, there is a known method described in PTL 1, for example. In the method described in PTL 1, an image of cells floating in a liquid inside a suspension culture vessel is acquired by means of an illumination device and an image acquisition device that are disposed outside the suspension culture vessel. Then, the particle-size distribution of the cells and the total number of cells are calculated through arithmetic processing using image analysis and parameters input in advance.

CITATION LIST

Patent Literature

{PTL 1} Japanese Unexamined Patent Application, Publication No. 2017-140006

SUMMARY OF INVENTION

According to one aspect, the present invention provides an observation device including: a stereo image-acquisition optical system that acquires images of cells floating in a culture fluid inside a culture vessel; and an analyzer that calculates a cell density of the cells on the basis of the images acquired by the stereo image-acquisition optical system, wherein the analyzer identifies a three-dimensional position of each of the cells included in the images and calculates the cell density on the basis of the number of cells present within a predetermined three-dimensional region.

According to another aspect, the present invention provides a cell observation method including: acquiring images of cells floating in a culture fluid inside a culture vessel; identifying a three-dimensional position of each of the cells included in the acquired images; and calculating the number of cells present within a predetermined three-dimensional region.

BRIEF DESCRIPTION OF DRAWINGS

FIG. 24 is a view showing a transverse section and a longitudinal section of an observation device according to a second modification of the fifth embodiment of the present invention.

DESCRIPTION OF EMBODIMENTS

First Embodiment

An observation device 1 according to a first embodiment of the present invention will be described below with reference to the drawings.

Figure 1:
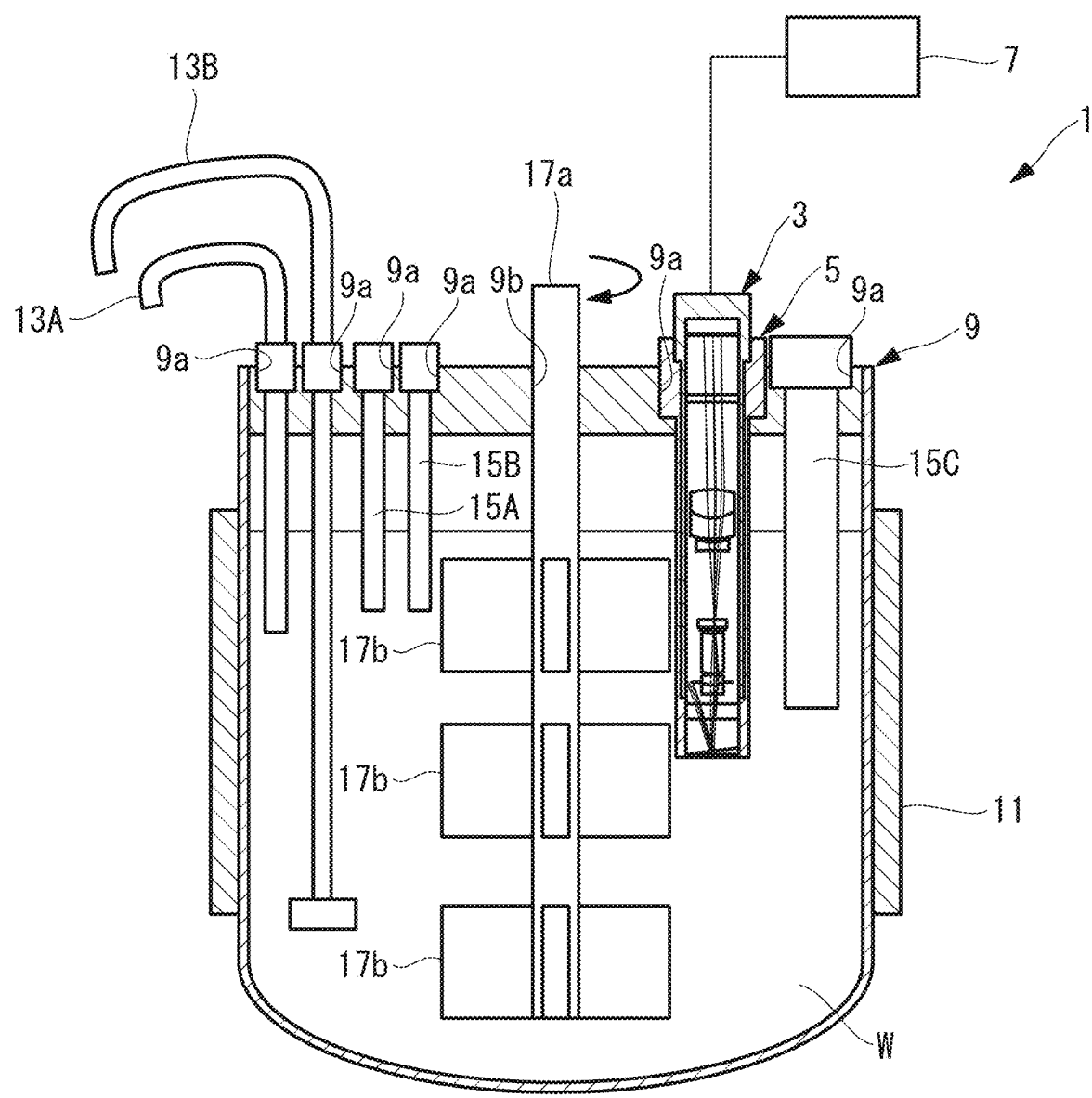
FIG. 1 is a longitudinal sectional view of an observation device according to a first embodiment of the present invention.
Figure 2:
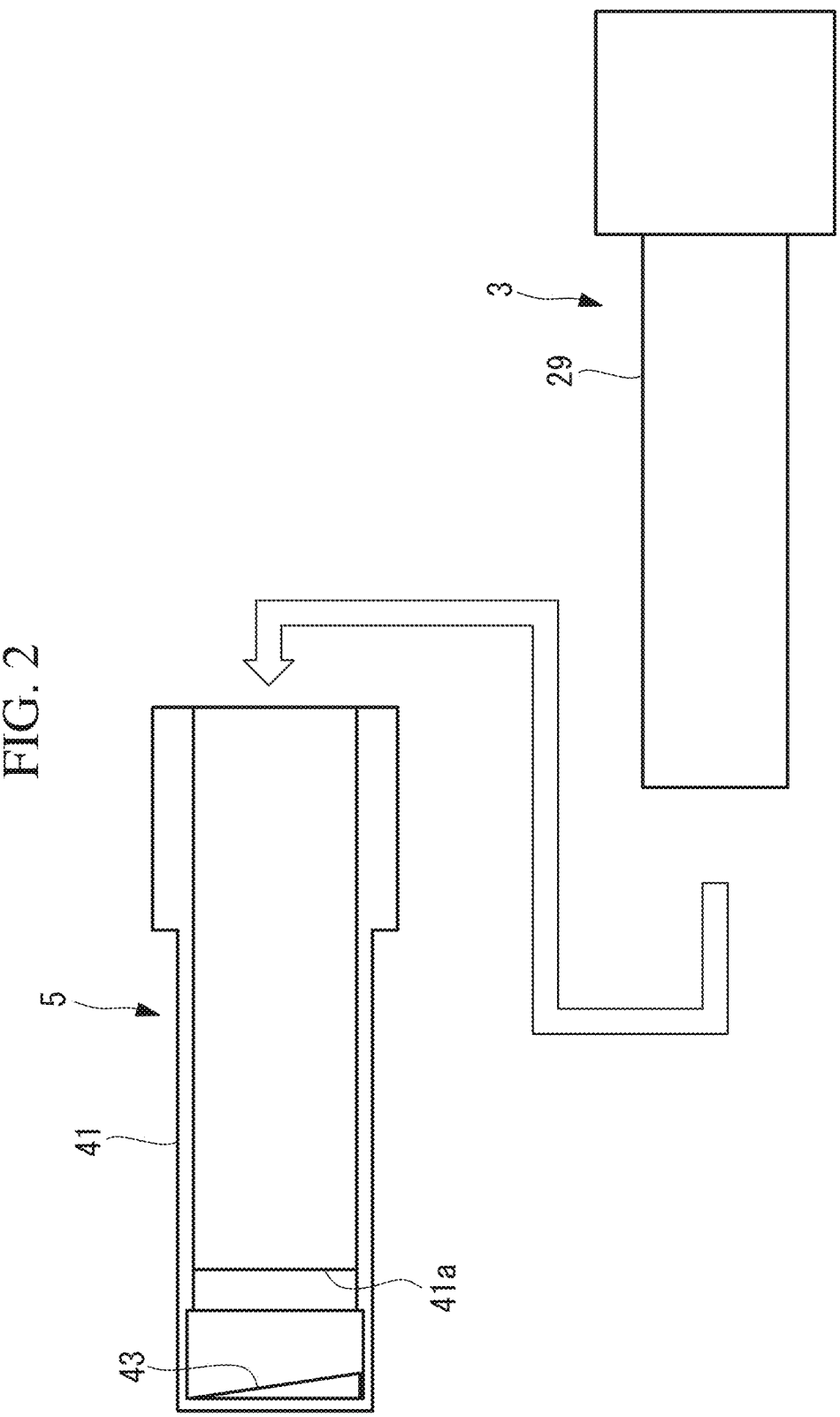
FIG. 2 is a longitudinal sectional view of a distal-end unit and a camera unit, which are shown in FIG. 1, before the distal-end unit is mounted thereon.

As shown in FIGS. 1 and 2, the observation device 1 of this embodiment includes: a camera unit 3 that is used to observe cells S (see FIG. 10 etc.) floating in a culture fluid (culture medium) W inside a culture vessel 9; a distal-end unit 5 that is detachably mounted on a distal end of the camera unit 3; and an image analysis unit 7 that calculates the cell density in the culture fluid W.

The culture vessel 9 is a bottomed cylindrical bioreactor whose upper surface is closed, and accommodates the cells S therein together with the culture fluid W. The circumference of the culture vessel 9 is surrounded by a cylindrical temperature adjustment jacket 11 that adjusts the temperature of the culture fluid W. The culture vessel 9 has, in the upper surface, a plurality of ports 9a through which various hoses 13 and probes 15 are inserted and an insertion port 9b through which a stirring mechanism 17 is inserted.

In the example shown in FIG. 1, six ports 9a are provided in the upper surface of the culture vessel 9. A culture-medium transport hose 13A for transporting the culture fluid W, an air supply hose 13B for supplying air to the culture fluid W, a pH probe 15A for measuring the pH of the culture fluid W, a temperature measurement probe 15B for measuring the temperature of the culture fluid W, and a $CO_2$ pressure probe 15C for measuring the $CO_2$ pressure of the culture fluid W are inserted through the ports 9a. The camera unit 3, with the distal-end unit 5 being mounted thereon, can be inserted through the other one of the ports 9a of the culture vessel 9.

The stirring mechanism 17 includes: a stirring shaft 17a that is inserted into the culture vessel 9 through the insertion port 9b of the culture vessel 9; and a plurality of stirring blades 17b that are provided on the stirring shaft 17a. The plurality of stirring blades 17b are disposed at three places on the stirring shaft 17a in the longitudinal direction, and some of the stirring blades 17b are disposed, at each of the three places, at intervals in the circumferential direction.

The stirring mechanism 17 can stir the culture fluid W when the stirring shaft 17a and the stirring blades 17b are rotated about a longitudinal axis by a drive unit (not shown), such as a motor. Then, the stirring mechanism 17 stirs the culture fluid W, thereby preventing the cells S from sticking on an inner surface of the culture vessel 9 and making it possible to culture the cells S while causing the cells S to float in the culture fluid W.

Figure 3:
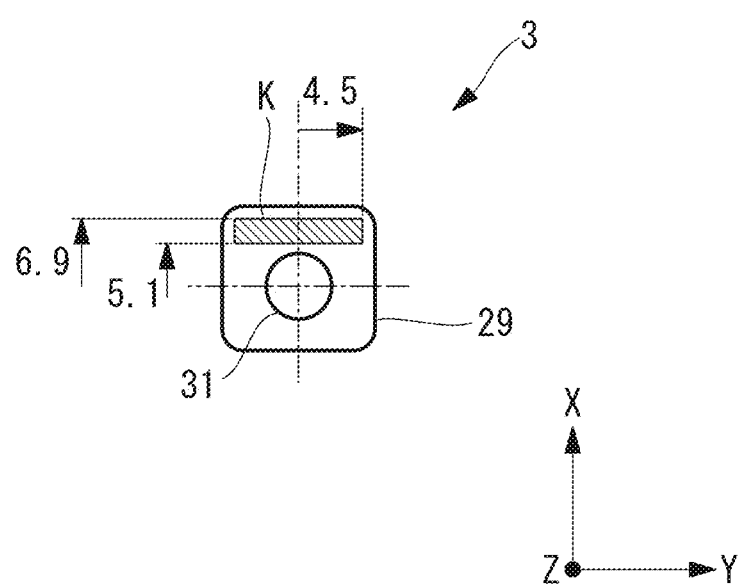
FIG. 3 is a front view of the camera unit shown in FIG. 2, viewed from the distal end along the longitudinal direction.
Figure 4:
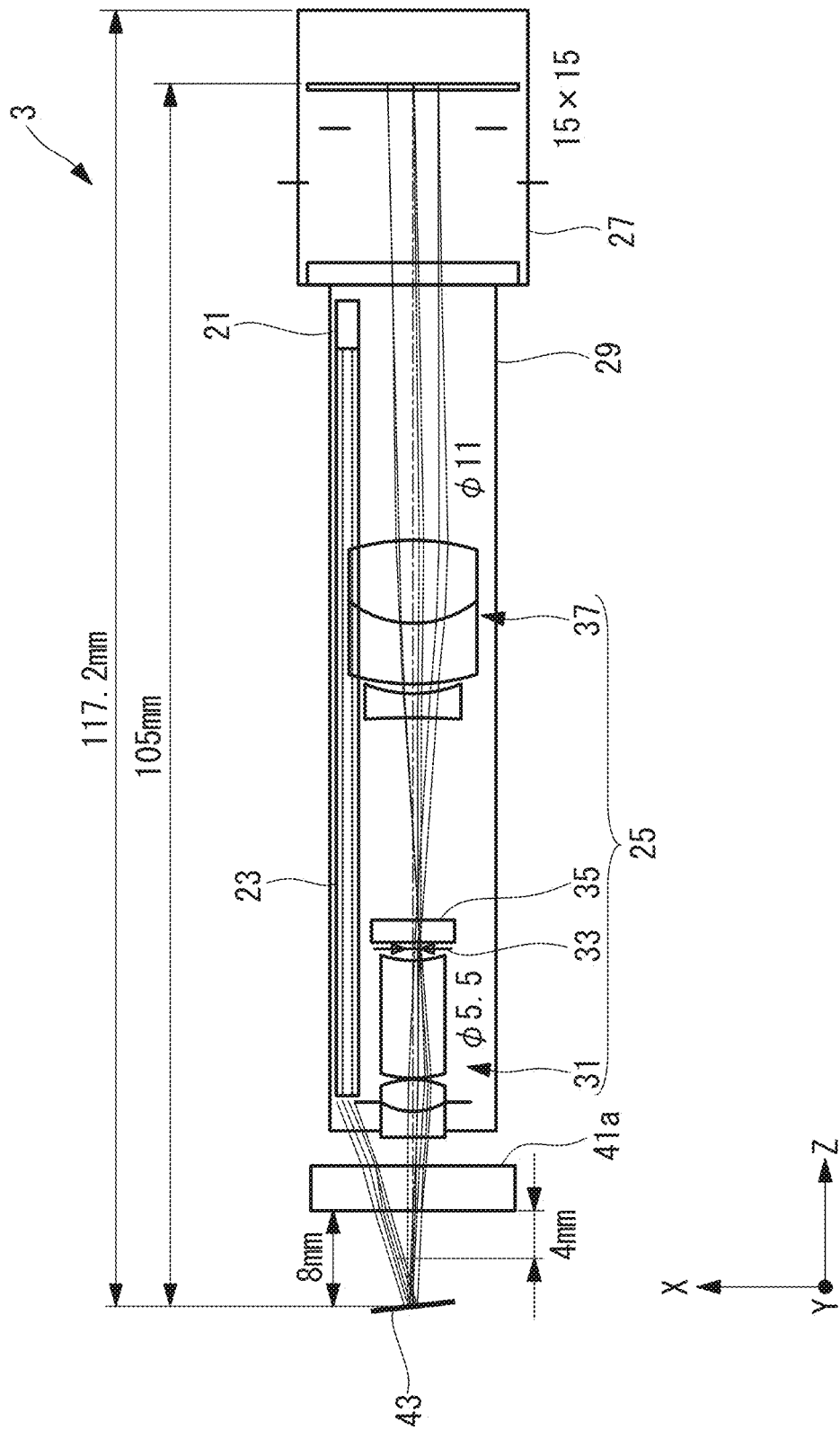
FIG. 4 is a view showing an X-Z cross section of the camera unit shown in FIG. 2.
Figure 5:
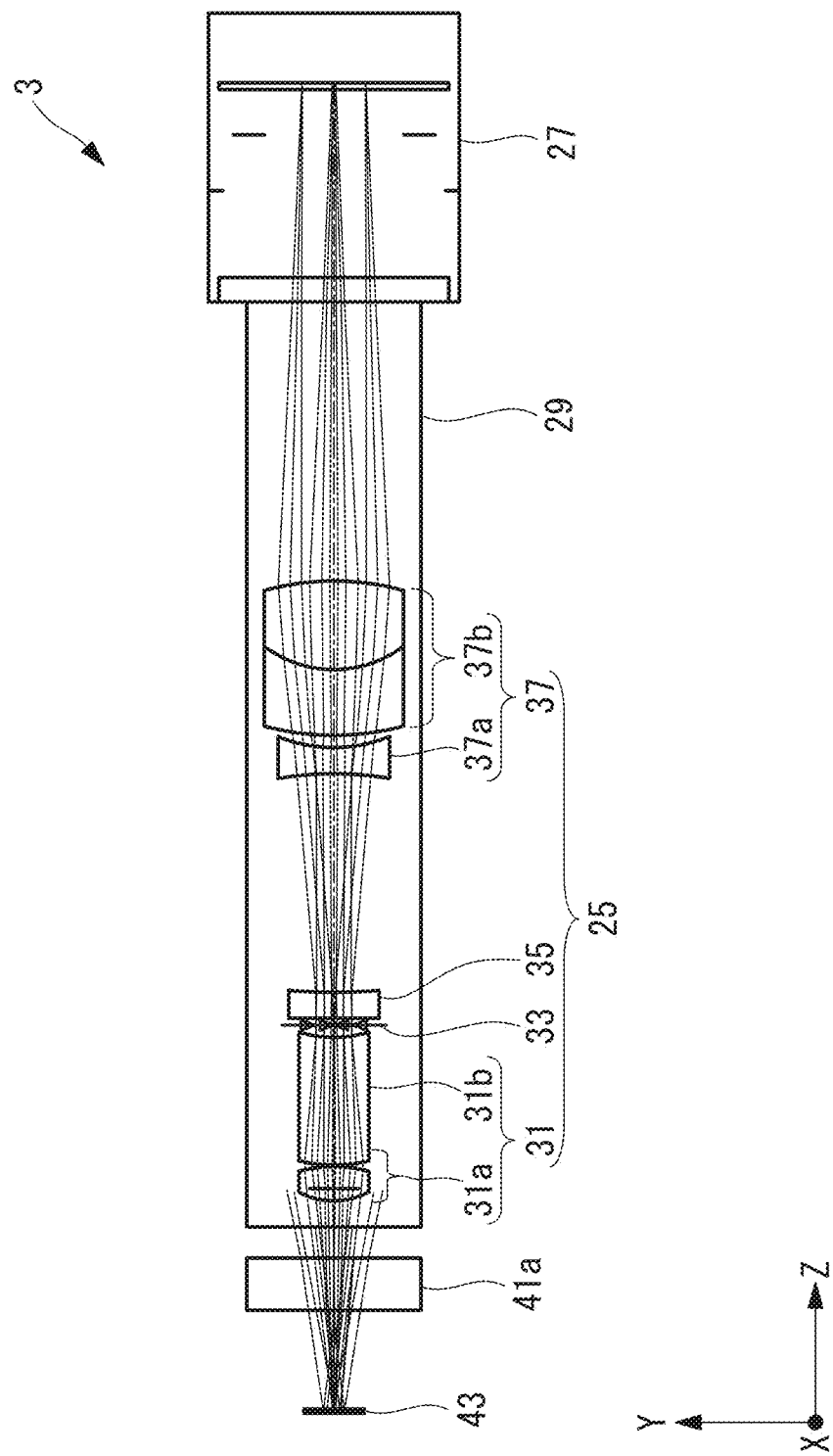
FIG. 5 is a view showing a Y-Z cross section of the camera unit shown in FIG. 2.

As shown in FIGS. 3, 4, and 5, the camera unit 3 includes: a light source 21; a light guide fiber 23 that guides illumination light emitted from the light source 21; a stereo optical system (stereo image-acquisition optical system) 25 that forms, for the same cell S, two views with parallax due to being viewed from different viewpoints; an image-acquisition device (stereo image-acquisition optical system) 27 that acquires images of the two views formed by the stereo optical system 25; and an elongated substantially square-tubular casing 29 that accommodates the light source 21, the stereo optical system 25, and the image-acquisition device 27. In FIG. 3, reference sign K denotes a light emission area.

The light source 21 is disposed at a position close to a base end of the casing 29.

The light guide fiber 23 guides illumination light emitted from the light source 21 to a distal end of the casing 29.

The stereo optical system 25 includes, in order from the distal end, an objective optical system 31 that focuses light from the cells S, an aperture opening part 33 that splits the light focused by the objective optical system 31, a deflecting prism 35 that deflects the respective light rays obtained after the splitting at the aperture opening part 33, and an imaging optical system 37 that images the respective light rays deflected by the deflecting prism 35.

The stereo optical system 25 has, for example, a magnification of 4-times and an NA of 0.089. Furthermore, the stereo optical system 25 has a real field of view of 1.06 mm in the X-direction and 0.6 mm in the Y-direction. The stereo optical system 25 forms images in stereo in the Y-direction. Hereinafter, the arrangement direction of the viewpoints of the stereo optical system 25 is referred to as a stereo direction. Furthermore, it is assumed that the direction along the optical axis of the stereo optical system 25 is the Z-direction, and the direction perpendicular to the optical axis of the stereo optical system 25 and perpendicular to the stereo direction is the X-direction.

Figure 6:
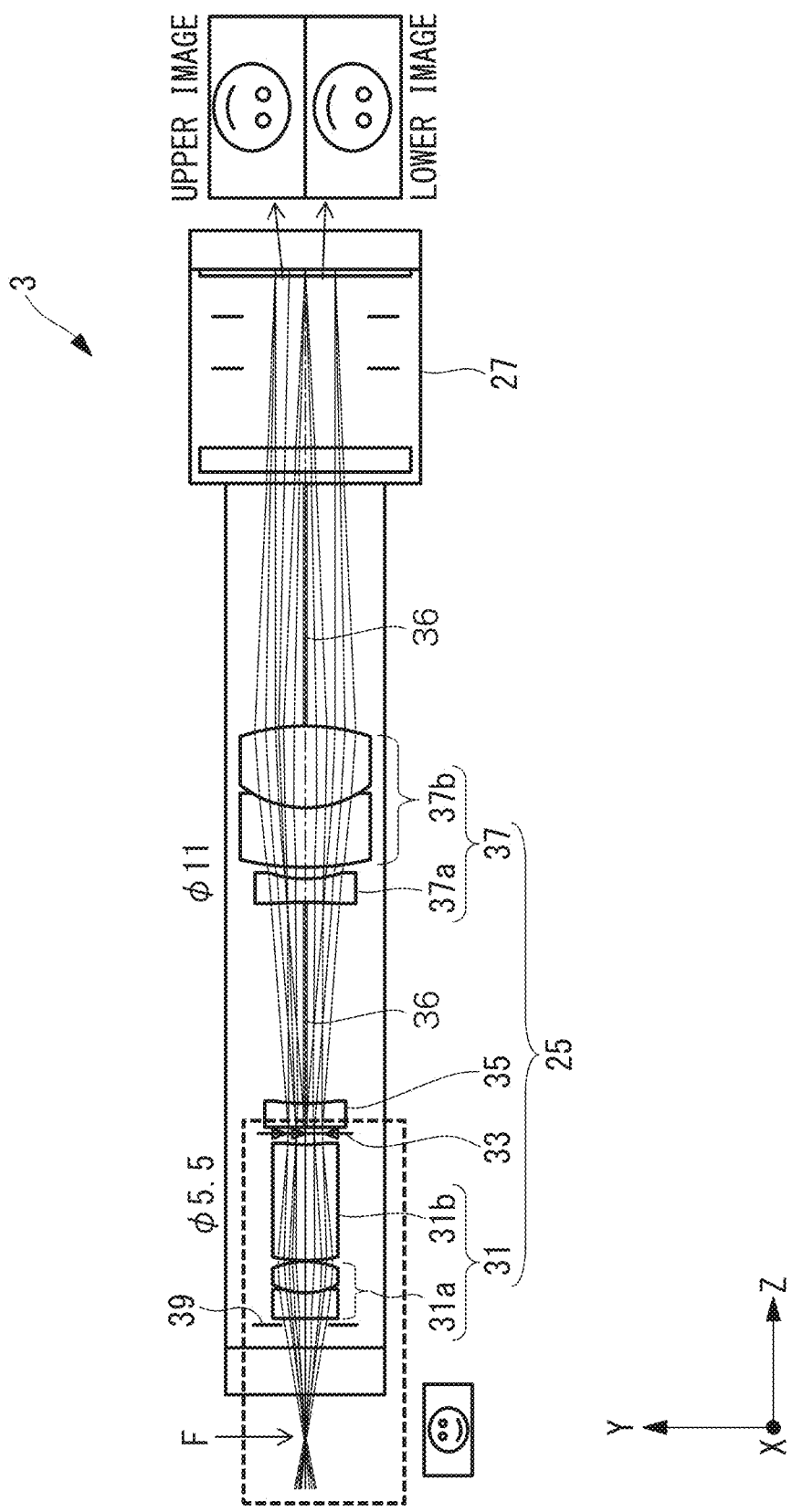
FIG. 6 is a view showing the Y-Z cross section of the camera unit shown in FIG. 2.
Figure 7:
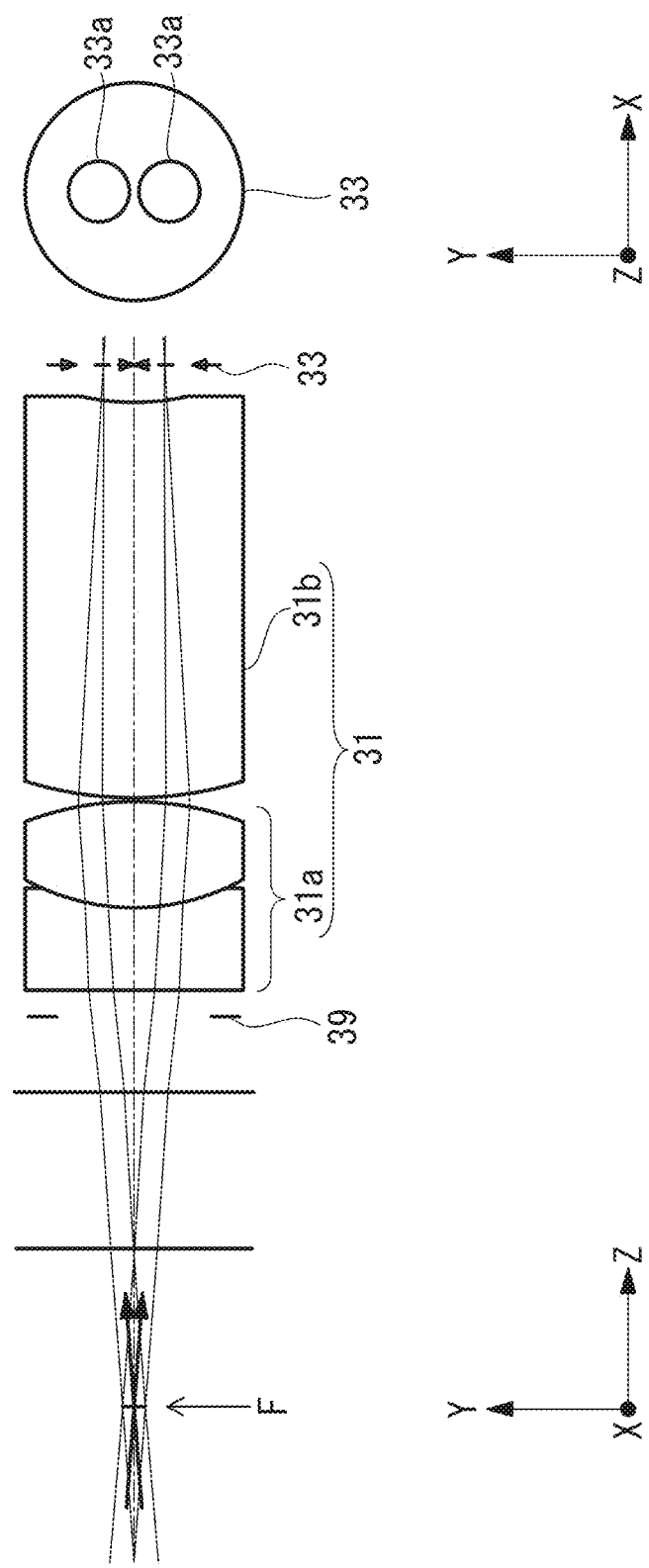
FIG. 7 is a longitudinal sectional view showing the vicinity of a distal end of the camera unit shown in FIG. 6.

As shown in FIGS. 6 and 7, the objective optical system 31 is composed of: a lens component 31a that is obtained by combining a biconcave lens and a biconvex lens; and a convex-concave lens 31b. The objective optical system 31 has, for example, a diameter of 5.5 mm. Furthermore, the objective optical system 31 has, for example, a working distance (WD) of 4 mm. In FIGS. 6 and 7, reference sign F denotes the position of the best focus plane, and reference sign 39 denotes a cover glass. In FIG. 7, chief rays are mainly shown.

As shown in FIG. 7, the aperture opening part 33 is disposed at the pupil position. In the aperture opening part 33, two holes 33a that each have, for example, a diameter of 1.4 mm are provided with a gap therebetween in the stereo direction.

Figure 8:
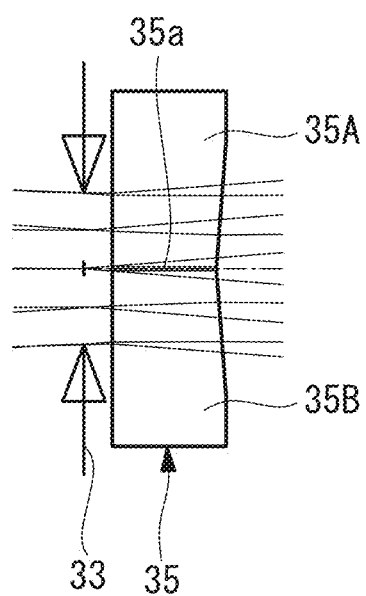
FIG. 8 is an enlarged view of a deflecting prism shown in FIG. 6.

As shown in FIG. 8, for example, the deflecting prism 35 is obtained by bonding a prism 35A and a prism 35B, whose surfaces that are close to the image-acquisition device 27 have planes inclined in directions in which the thicknesses increase as the absolute values in the Y-direction become larger. The surfaces that are close to the image-acquisition device 27, for example, are inclined at an angle of 2.9° in the +Y-direction and an angle of −2.9° in the −Y-direction, with respect to the optical axis. Furthermore, light-blocking paint 35a through which light is not transmitted is applied between the prism 35A and the prism 35B. Instead of the light-blocking paint 35a, a light-blocking member may be provided between the prism 35A and the prism 35B.

As shown in FIGS. 5 and 6, the imaging optical system 37 is composed of: a biconcave lens 37a; and a lens composition 37b that is obtained by combining a convex-concave lens and a biconvex lens. The imaging optical system 37 has a diameter of 11 mm. As shown in FIG. 6, light-blocking members 36 that prevent mixing of light passing in the +Y-direction and light passing in the −Y-direction are provided between the deflecting prism 35 and the imaging optical system 37 and between the imaging optical system 37 and the image-acquisition device 27.

The image-acquisition device 27 is disposed at a position closest to the base end of the casing 29. The image-acquisition device 27 has an image-acquisition area of 4.28 mm in the X-direction and 5.9 mm in the Y-direction. Image information about cells that is acquired by the image-acquisition device 27 is sent to the image analysis unit 7.

As shown in FIG. 2, the distal-end unit 5 includes: a substantially square-tubular protective cover 41 into which the camera unit 3 is inserted; and a mirror (oblique illumination part) 43 that radiates illumination light onto the cells S at an angle in a direction intersecting the stereo direction. The protective cover 41 is subjected to sterilization process, and the distal-end unit 5 can be replaced as a disposable part that is thrown away after single use.

The protective cover 41 has, at a position closer to a base end thereof than a distal end thereof is, open windows 41a that are open in side surfaces opposed to each other in the width direction. These open windows 41a are disposed between the mirror 43 and the objective optical system 31 in a state in which the camera unit 3 has been inserted into the protective cover 41. Furthermore, the open windows 41a each have such a size as to allow the cells S and the culture fluid W to pass through the inside of the protective cover 41 in the width direction. These open windows 41a may also be, for example, opening sections formed by dividing the protective cover 41 into a distal-end section and a base-end section in the longitudinal direction and connecting the distal-end section and the base-end section at two places in the circumferential direction of the protective cover 41.

The mirror 43 is disposed at the distal end of the protective cover 41 so as to face the base end thereof. Furthermore, a reflective surface of the mirror 43 has an inclination of 6.5° with respect to the optical axis of the objective optical system 31. The mirror 43 reflects, for example, illumination light guided by the light guide fiber 23 toward the objective optical system 31 in the camera unit 3 at an angle in a direction perpendicular to the stereo direction, thereby obliquely illuminating the cells S in the culture fluid W.

Figure 9:
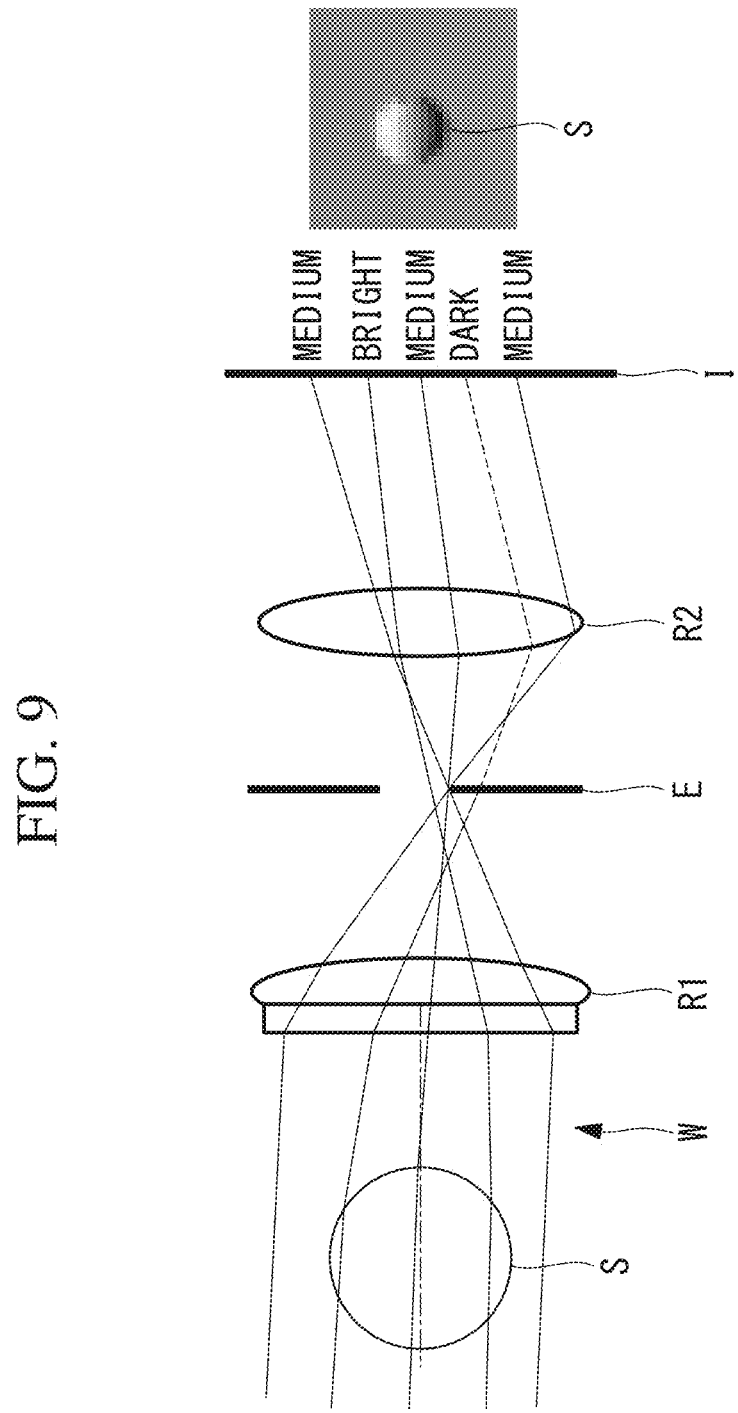
FIG. 9 is a view for explaining how to add contrast through oblique illumination.

Because the refractive indexes are different in the culture fluid W and inside the cell S, light is bent at the boundary between the culture fluid W and the cell S. As shown in FIG. 9, for example, a region corresponding to light that is bent in such a direction as to pass through the outside of a pupil E becomes dark in an image plane I, and a region corresponding to light that is bent in such a direction as to pass through the inside of the pupil E becomes bright in the image plane I. Therefore, the cells S are obliquely illuminated by using the mirror 43, thereby making it possible to acquire an image in which the contrast of the cells S has been improved. In FIGS. 9, R1 and R2 denote lenses.

The image analysis unit 7 identifies the positions of the cells S included in images of the two views, the images being acquired by the image-acquisition device 27. Then, the image analysis unit 7 calculates the cell density in the culture fluid W on the basis of the number of cells S present in a predetermined region. The predetermined region is, for example, a range in focus and is set in advance. In this embodiment, it is preferred that the predetermined region be within a range of Z±0.2 mm in the distance from the best focus position in the Z-direction, for example.

Next, the operation of the observation device 1 of this embodiment will be described below.

In order to observe the cells S, which are cultured while being made to float in the culture fluid W inside the culture vessel 9, by using the observation device 1, which has the above-described configuration, first, as shown in FIG. 1, in a state in which the distal-end unit 5 has been mounted on the camera unit 3, the camera unit 3 and the distal-end unit 5 are inserted into the culture fluid W through the port 9a of the culture vessel 9.

Next, illumination light is generated by the light source 21 in the camera unit 3, the illumination light is guided by the light guide fiber 23, and the illumination light is emitted from the distal end of the light guide fiber 23 toward the mirror 43 in the distal-end unit 5. Accordingly, the illumination light reflected by the mirror 43 is radiated onto the cells S that have passed through the open window 41a, while floating in the culture fluid W, and have entered the distal-end unit 5. Then, transmitted light of the illumination light that has been transmitted through the cells S enters the stereo optical system 25 in the camera unit 3.

In the stereo optical system 25, the transmitted light of the illumination light that has been transmitted through the cells S is focused by the objective optical system 31 and is then split by the aperture opening part 33, and light rays obtained after the splitting are respectively deflected by the deflecting prism 35. Accordingly, two views with parallax, in which individual cells S are viewed from different viewpoints, are formed for a plurality of cells S floating in the culture fluid W. Then, images of the formed two views are acquired by the image-acquisition device 27.

Figure 10:
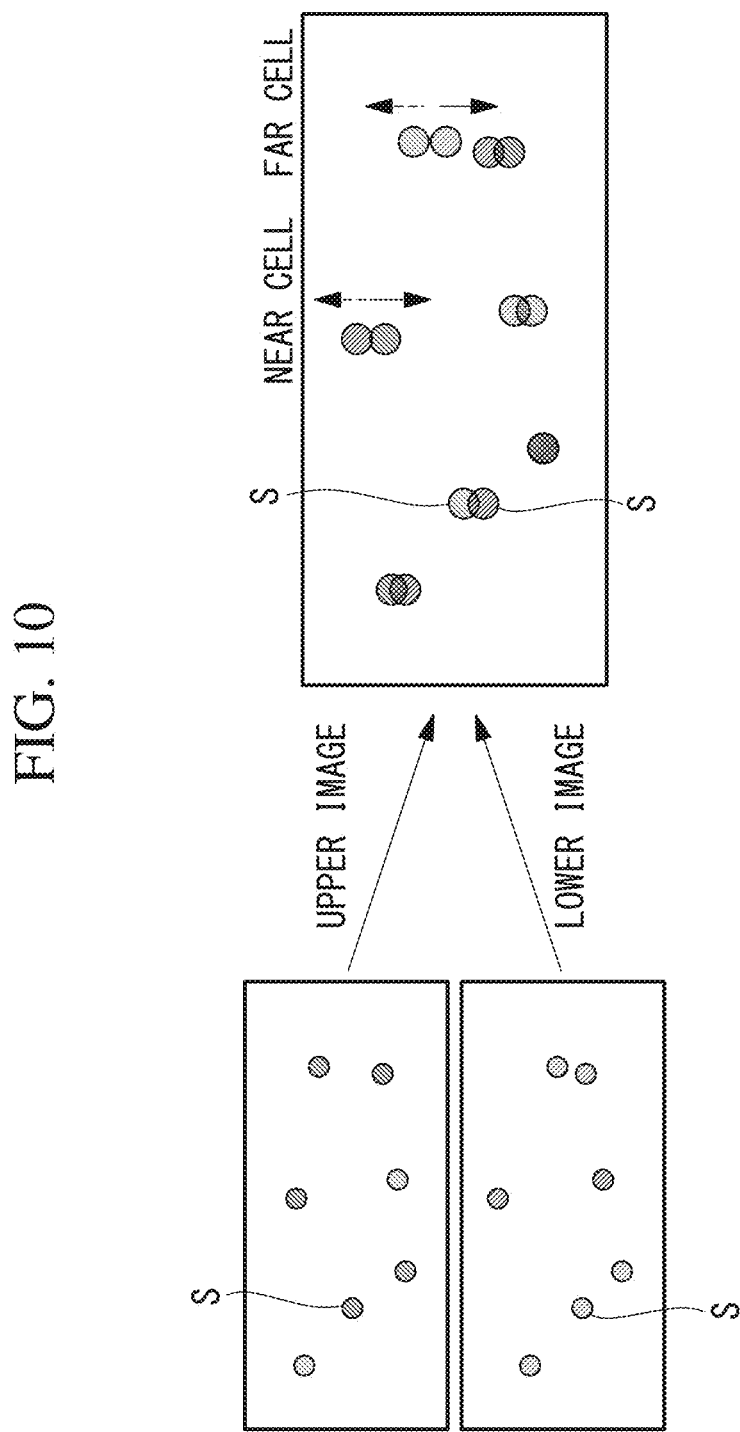
FIG. 10 is a view showing an upper image, a lower image, and a state in which the upper image and the lower image are superimposed.

Image information about each of the two views that is acquired by the image-acquisition device 27 is sent to the image analysis unit 7. Then, as shown in FIG. 10, the image analysis unit 7 generates, for the plurality of cells S, two 2D images with parallax, in which the individual cells S are viewed from different viewpoints, i.e., an upper image and a lower image that are shown in FIG. 10, on the basis of the input image information.

Next, the image analysis unit 7 identifies the positions of the respective cells S included in the generated two images of the plurality of cells S. Then, the image analysis unit 7 calculates the cell density in the culture fluid W on the basis of the number of cells S present in the predetermined region.

In this case, the stereo optical system 25 forms, for the plurality of cells S in the culture fluid W, two views with parallax, in which the individual cells S are viewed from different viewpoints, thereby causing a situation in which the position of the same cell S in the Y-direction is shifted, in the directions opposite from each other in accordance with the distance from the stereo optical system 25, between the images of the two views, the images being acquired by the image-acquisition device 27.

Figure 11:
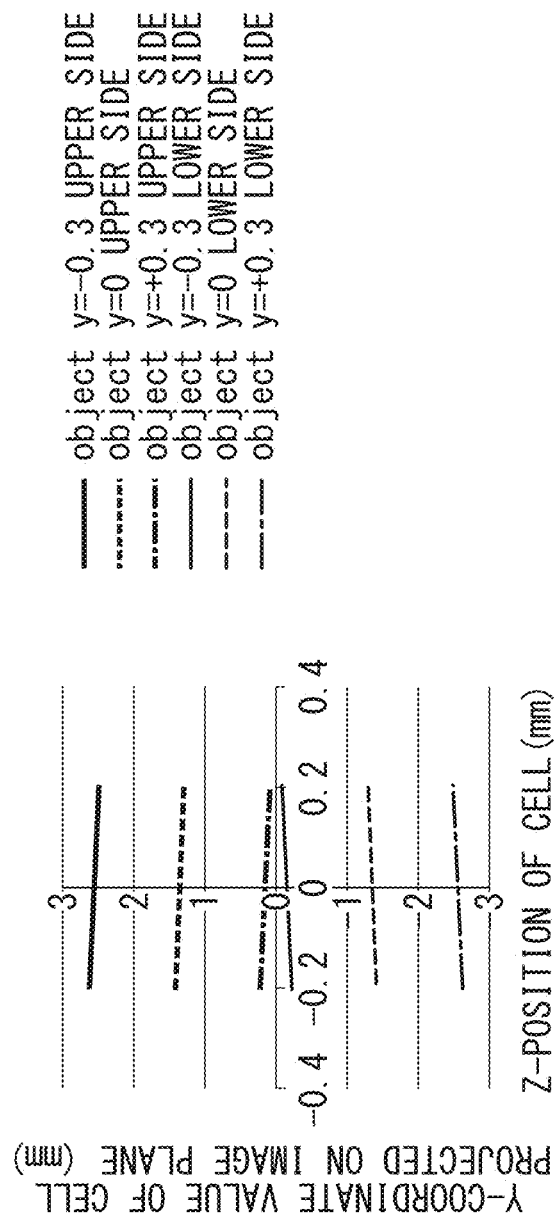
FIG. 11 is a view showing the relationship between the Y-coordinate of a cell projected on an image plane and the Z-position of the cell.
Figure 12:
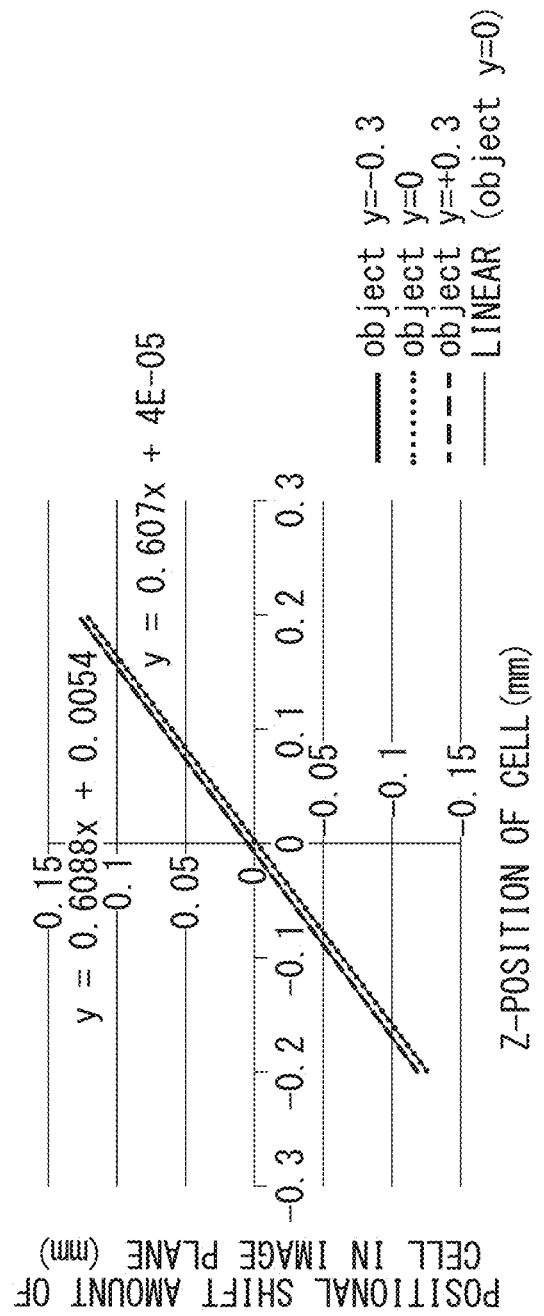
FIG. 12 is a view showing the relationship between a positional shift amount of a cell in the image plane and the Z-position of the cell.
Figure 13:
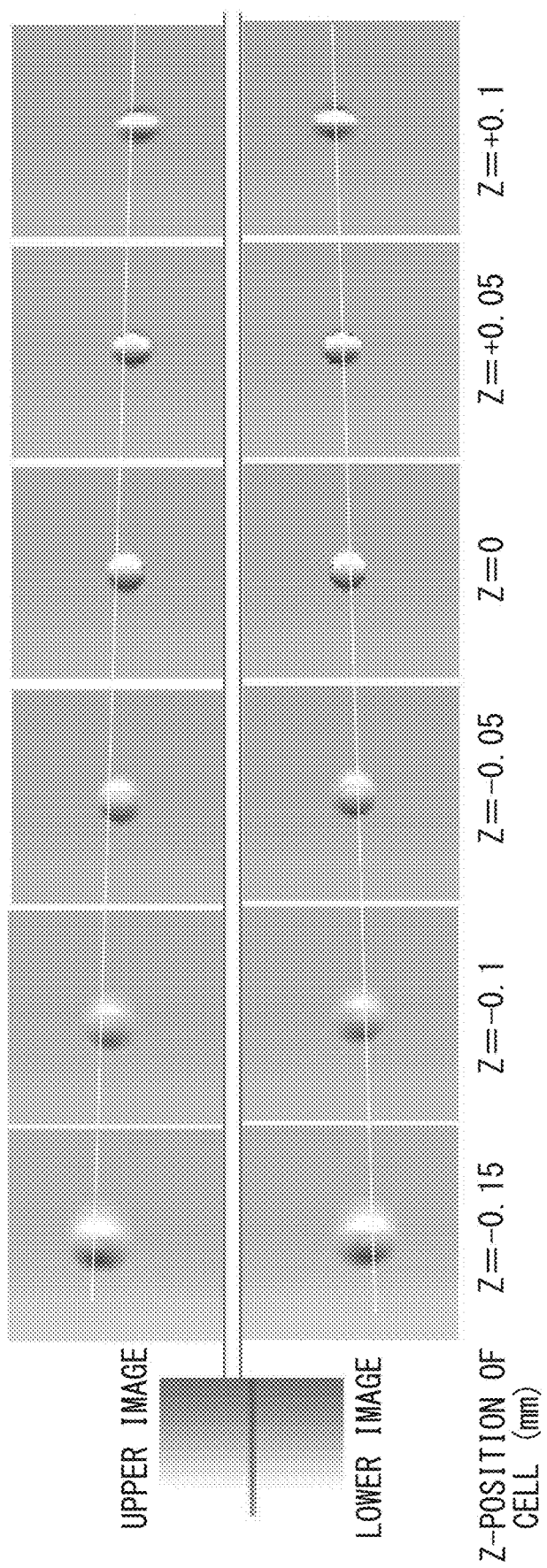
FIG. 13 is a view for explaining a state in which the positional shift amount of a cell is proportional to the focus position.

The shift amount δ is defined as ΔY-ΔY0, when ΔY0 is the difference in the Y-coordinate between two cell views in an imaging plane that are acquired through image formation of an identical cell S present in the best focus plane F, and ΔY is the difference in the Y-coordinate between two cell views in the imaging plane that are acquired through image formation of a cells S present at an arbitrary Z-position. Then, for example, as shown in FIGS. 10, 11, and 12, the shift amount between images becomes smaller, i.e., takes a more negative value, as the distance of a cell S from the stereo optical system 25 becomes closer, and the shift amount between images becomes larger as the distance of a cell S therefrom becomes farther. Specifically, as shown in FIG. 13, the positional shift amount of a cell S is proportional to the focus position. FIG. 13 shows a case in which the size of each cell S is 20 μm, the refractive index of the cell S is 1.36, the refractive index of the culture fluid W is 1.332, and the size of a display image is 0.48 mm×0.48 mm (corresponding to 0.12 mm×0.12 mm at the object side). The same conditions are applied to FIG. 14.

Therefore, because the three-dimensional positions of the respective cells S are found on the basis of the positional shift amounts of the respective cells S, the image analysis unit 7 can accurately distinguish between cells S that are included in the predetermined region and cells S that are not included therein and can calculate the cell density in the culture fluid W. Accordingly, according to the observation device 1 of this embodiment, it is possible to accurately measure the cell density in the culture fluid W regardless of the shape, the size, etc. of the culture vessel 9 to be used.

Figure 14:
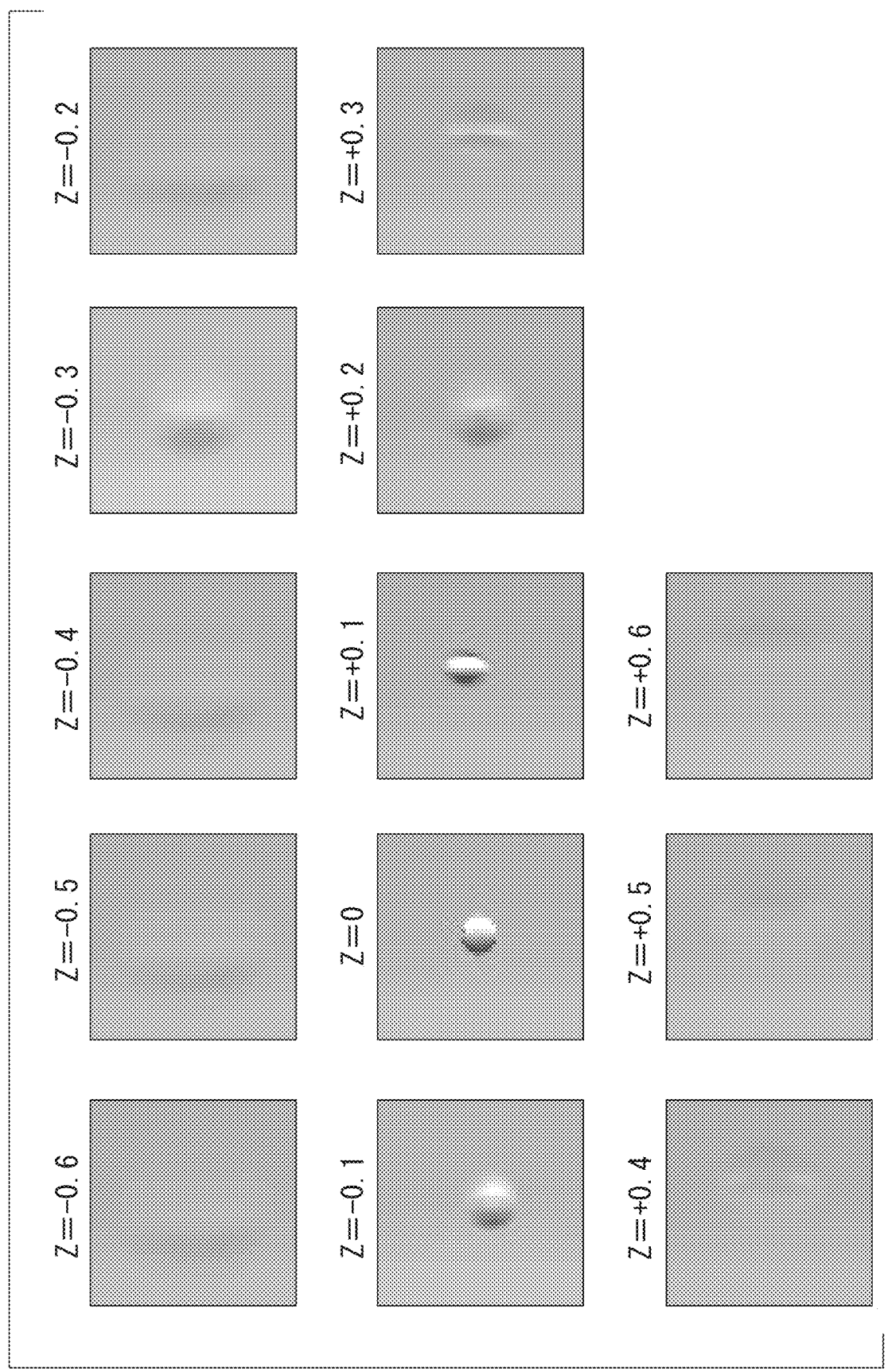
FIG. 14 is a view showing an example of changes in images with focus position.

As shown in FIG. 14, because images are significantly blurred when the distance from the best focus position exceeds Z±0.2 mm, the measurement is affected little. Other than the cell density, the sizes and the shapes of cells S and cell masses can also be measured at a position in focus. Accordingly, the states of the cells S can be grasped. In FIG. 14, the unit of Z is mm.

The volume of a region where the measurement can be performed by the stereo optical system 25 of this embodiment is the product of the real field of view in the X-direction, the real field of view in the Y-direction, and the range in focus in the Z-direction, i.e., 1.06 mm×0.6 mm×0.4 mm=0.2544 mm$^3$. Furthermore, the number of cells S in the region where the measurement can be performed by the stereo optical system 25 is $10^1$/mm$^3$×0.2544 mm$^3$=2.544 at minimum and $10^3$/mm$^3$×0.2544 mm$^3$=254.4 at maximum, for example.

Although the bioreactor culture vessel 9 is illustrated as a culture vessel in which the cells S are cultured, in this embodiment, the culture vessel may be a cell culture bag instead of the bioreactor. When a cell culture bag is used, the camera unit 3 and the distal-end unit 5 of the observation device 1 are inserted into the cell culture bag and are used. The same applies to a second embodiment and a third embodiment.

Second Embodiment

Next, an observation device according to a second embodiment of the present invention will be described below with reference to the drawings.

Figure 15:
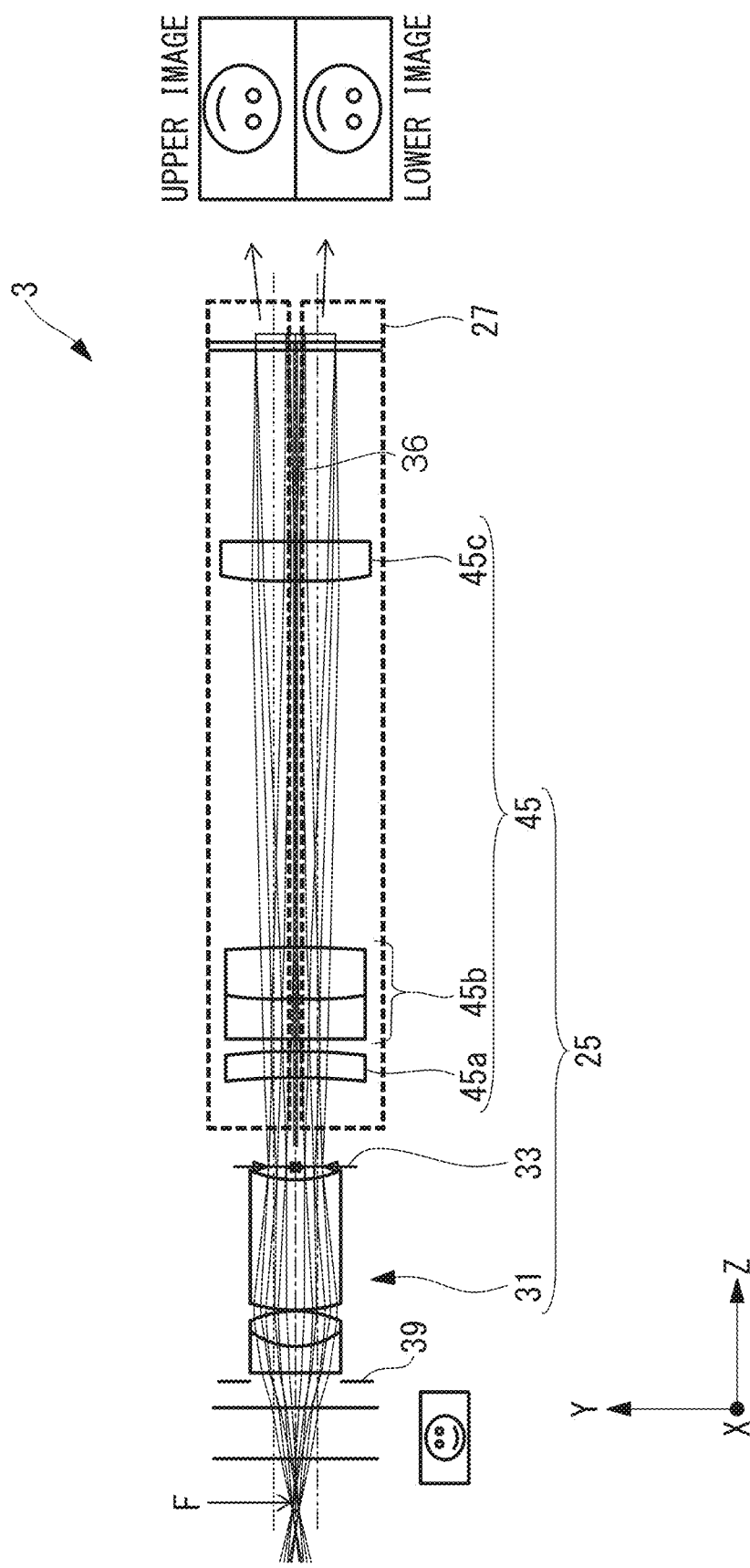
FIG. 15 is a view showing a Y-Z cross section of a camera unit according to a second embodiment of the present invention.
Figure 16:
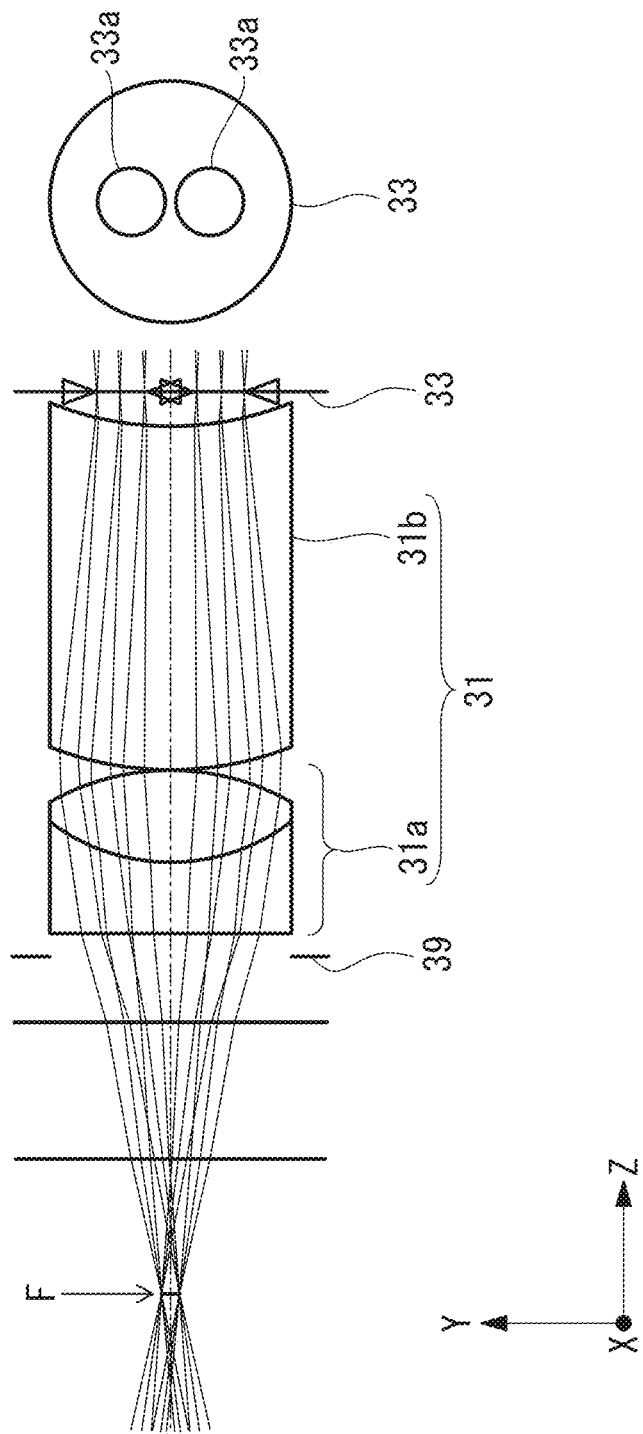
FIG. 16 is a longitudinal sectional view showing the vicinity of a distal end of the camera unit shown in FIG. 15.

As shown in FIGS. 15 and 16, the observation device 1 of this embodiment differs from that of the first embodiment in terms of the configuration of the stereo optical system 25.

In the description of this embodiment, identical reference signs are assigned to parts having configurations common to those of the observation device 1 of the above-described first embodiment, and a description thereof will be omitted.

The stereo optical system 25 of this embodiment does not include the deflecting prism 35 but includes the objective optical system 31, which focuses light from the cells S, the aperture opening part 33, which splits the light focused by the objective optical system 31, and an imaging optical system 45 that separately images the respective light rays obtained after the splitting at the aperture opening part 33.

The imaging optical system 45 is composed of: a concave-convex lens 45a; a lens component 45b that is obtained by combining a biconcave lens and a biconvex lens; and a convex-concave lens 45c. The concave-convex lens 45a, the lens component 45b, and the convex-concave lens 45c are each composed of a left-and-right lens pair. The light-blocking member 36 is sandwiched between each of the lens pairs. The lens pair of each of the concave-convex lens 45a, the lens component 45b, and the convex-concave lens 45c has optical axes disposed on the left and right with a gap therebetween, thus allowing the respective light rays obtained after the splitting at the aperture opening part 33 to be transmitted therethrough.

In the observation device 1 of this embodiment that includes the stereo optical system 25 having the above-described configuration, the same effects as in the first embodiment are also afforded.

Third Embodiment

Next, an observation device according to a third embodiment of the present invention will be described below with reference to the drawings.

Figure 17:
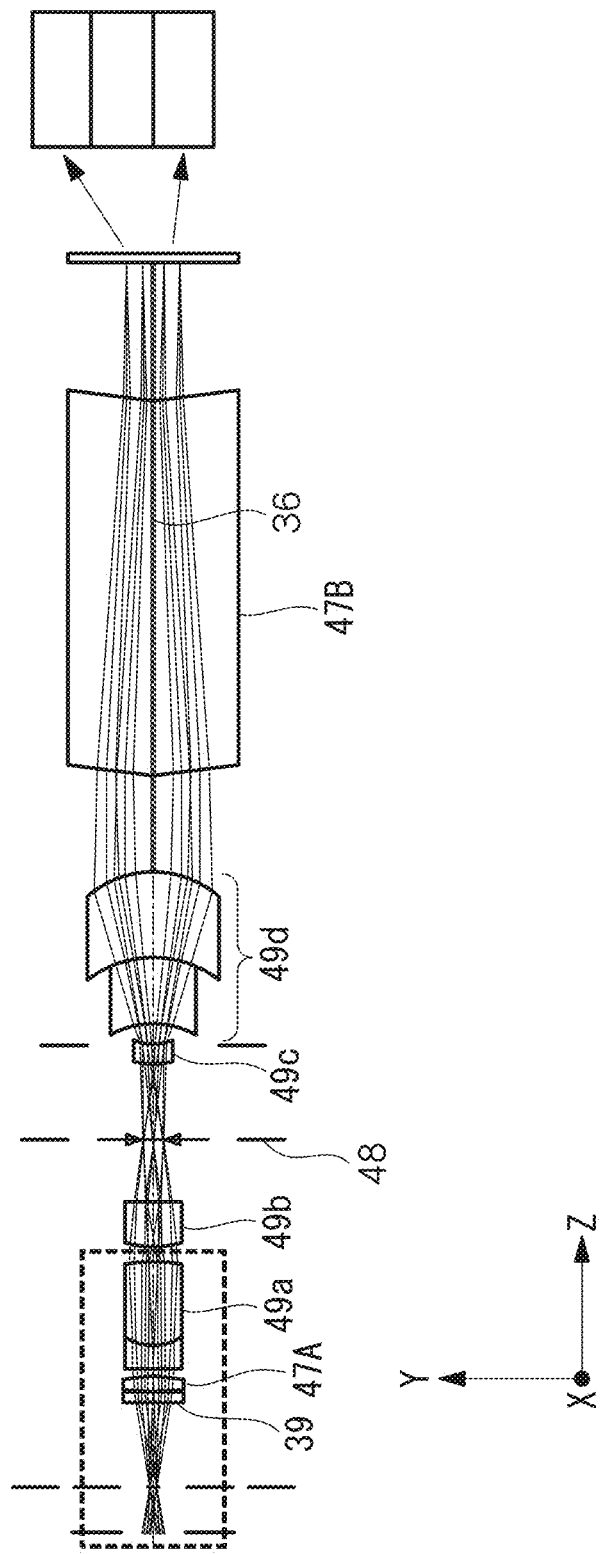
FIG. 17 is a view showing a Y-Z cross section of a camera unit according to a third embodiment of the present invention.
Figure 18:
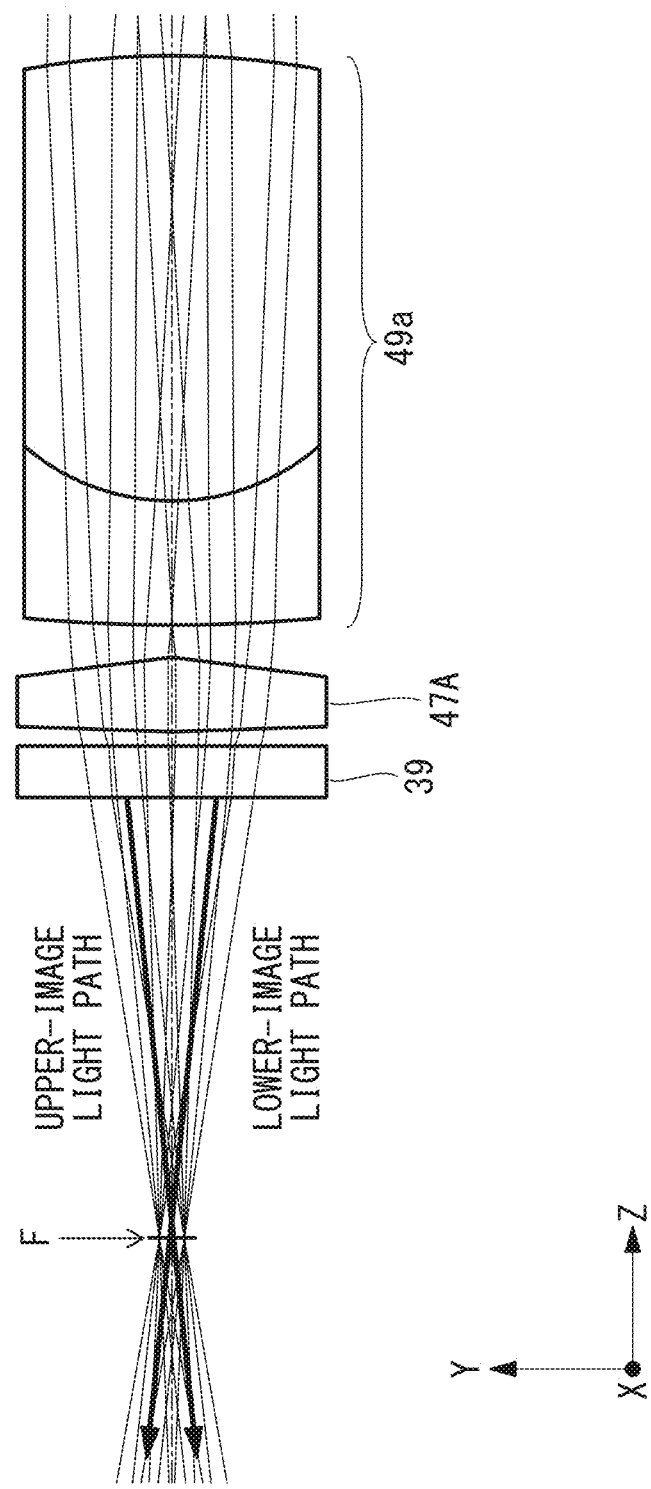
FIG. 18 is a longitudinal sectional view showing the vicinity of a distal end of the camera unit shown in FIG. 17.

As shown in FIGS. 17 and 18, the observation device 1 of this embodiment differs from that of the first embodiment in terms of the configuration of the stereo optical system 25.

In the description of this embodiment, identical reference signs are assigned to parts having configurations common to those of the observation device 1 of the above-described first embodiment, and a description thereof will be omitted.

The stereo optical system 25 of this embodiment includes a distal-end prism (prism) 47A that splits light from the cells S into two views. Furthermore, the stereo optical system 25 includes, instead of the aperture opening part 33, an aperture opening part 48 that has a single opening, which is not split into two. The stereo optical system 25 has, for example, a magnification of 4-times and an NA of 0.087. Furthermore, the stereo optical system 25 has a real field of view of 1.07 mm in the X-direction and 0.5 mm in the Y-direction.

In FIGS. 17 and 18, reference sign 49a denotes a lens component obtained by combining a convex-concave lens and a biconvex lens, reference sign 49b denotes a biconvex lens, reference sign 49c denotes a concave-convex lens, reference sign 49d denotes a lens component obtained by combining a concave-convex lens and a concave-convex lens, and reference sign 47B denotes a base-end prism.

The distal-end prism 47A and the base-end prism 47B each have a fixed thickness in the depth direction of FIG. 18.

Furthermore, the distal-end prism 47A has an incident surface having a tilt angle of −2° and an emission surface having a tilt angle of 7°, and is line symmetric with respect to the optical axis between the +Y side and the −Y side. Accordingly, the angles of chief rays entering the aperture opening part 48 on the +Y side and the −Y side have tilts in the directions opposite from each other, thus realizing a stereo optical system.

In the base-end prism 47B, the incident surface and the emission surface are formed parallel to each other, the incident surface has a tilt angle of 7°, and the emission surface has a tilt angle of 7°. Furthermore, the base-end prism 47B is composed of a base-end prism 47B1 and a base-end prism B2 that are line symmetric with respect to the optical axis between the +Y side and the −Y side.

The base-end prism 47B brings a +Y-side view and a −Y-side view close to each other, thereby allowing a single image-acquisition device (not shown) to acquire images of stereo views at the same time. If the base-end prism 47B is not provided, the distance between the position of the +Y-side view and the position of the −Y-side view is increased too much in the Y-direction, thus generating a wasteful area that is unnecessary for density analysis, near an intermediate point, i.e., near the optical axis, and it becomes necessary to use an image-acquisition device that has a wide image-acquisition area.

The light-blocking member 36, which prevents mixing of rays on the +Y side and rays on the −Y side, is provided between the combined lens component 49d and the image-acquisition device (not shown).

In the observation device 1 of this embodiment that includes the stereo optical system 25 having the above-described configuration, the same effects as in the first embodiment are also afforded.

Fourth Embodiment

Next, an observation device according to a fourth embodiment of the present invention will be described below with reference to the drawings.

Figure 19:
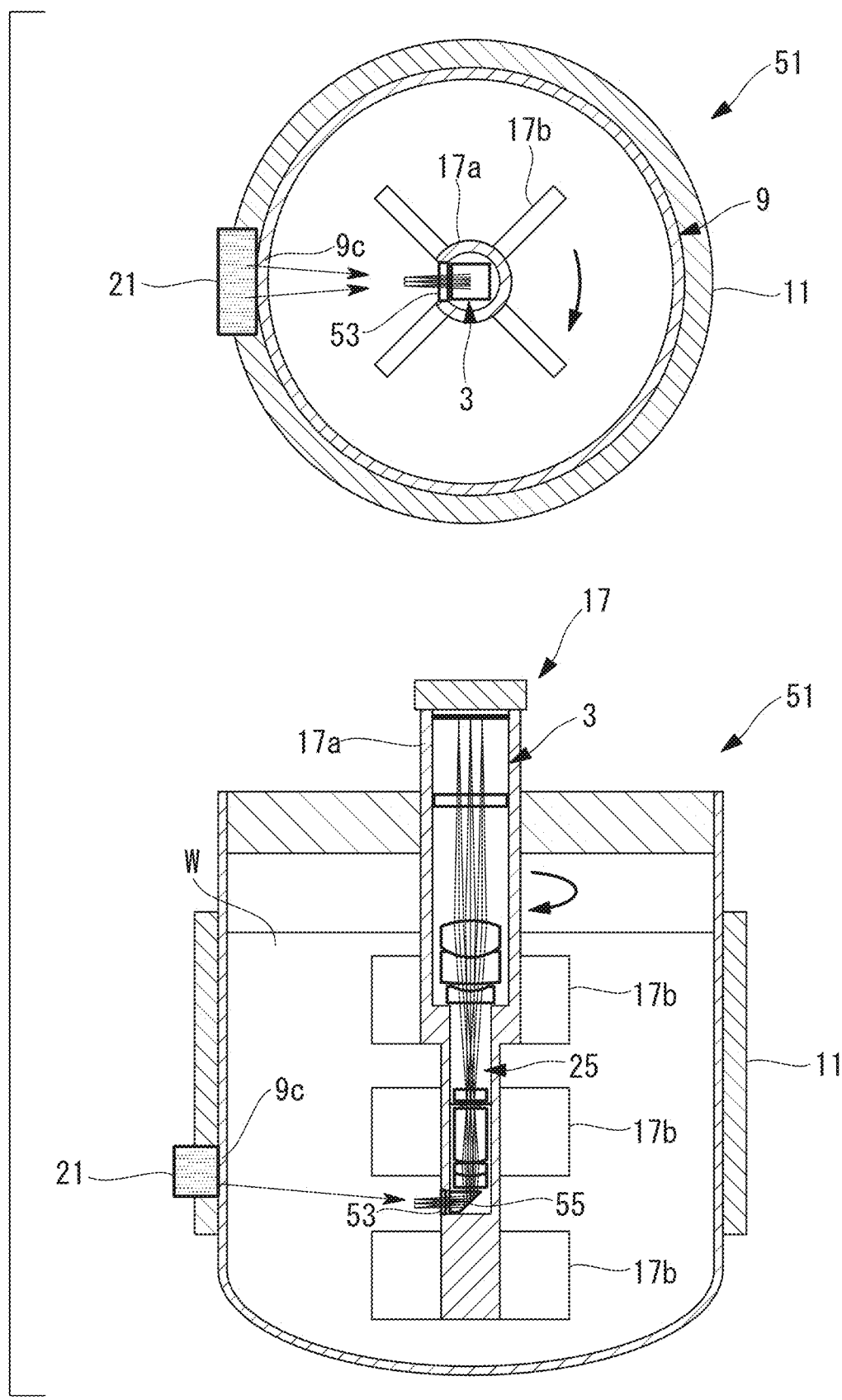
FIG. 19 is a view showing a transverse section and a longitudinal section of an observation device according to a fourth embodiment of the present invention.

As shown in FIG. 19, for example, an observation device 51 of this embodiment differs from those of the first to third embodiments in that the light source 21 is disposed outside the camera unit 3.

In the description of this embodiment, identical reference signs are assigned to parts having configurations common to those of the observation devices 1 of the above-described first to third embodiments, and a description thereof will be omitted. In this embodiment, a description will be given by illustrating the stereo optical system 25 of the above-described first embodiment.

As shown in FIG. 19, in the observation device 51 of this embodiment, the stirring shaft 17a is formed of a hollow cylindrical member. The camera unit 3 does not include the light source 21 and the light guide fiber 23 and is accommodated inside the stirring shaft 17a, without the distal-end unit 5 being mounted thereon.

Furthermore, the stirring shaft 17a has a parallel-plate observation window 53 that is made of an optically transparent material. The observation window 53 is disposed, for example, between the first stirring blade 17b and the second stirring blade 17b from the distal end of the stirring shaft 17a.

The stereo optical system 25 is disposed along the longitudinal direction of the stirring shaft 17a and images light from the cells S that has been transmitted through the observation window 53 and that has entered the stirring shaft 17a. Furthermore, the stereo optical system 25 is not rotated about the stirring shaft 17a.

A right-angle prism 55 that deflects light that has entered the stirring shaft 17a through the observation window 53, in the longitudinal direction of the stirring shaft 17a, is disposed between the observation window 53 and the stereo optical system 25. With the right-angle prism 55, the light that has entered the stirring shaft 17a through the observation window 53 enters the stereo optical system 25.

The light source 21 is disposed outside the culture vessel 9 and emits illumination light from the outside of the culture vessel 9 toward the observation window 53. Furthermore, the light source 21 is disposed so as to be shifted in height from the observation window 53. Furthermore, a lateral-direction (stereo direction=direction in which parallax occurs) light-emission area of the light source 21 is set wider than the width in which chief rays in the field of view of the stereo optical system 25 arrive. Accordingly, the cells S can be obliquely illuminated, thus making it possible to acquire an image in which the contrast of the cells S has been improved.

The culture vessel 9 has, in a side surface thereof, a parallel-plate illumination window 9c through which illumination light emitted from the light source 21 is transmitted. Accordingly, illumination light emitted from the light source 21 is transmitted through the illumination window 9c and is radiated onto the cells S in the culture fluid W. Then, transmitted light of the illumination light that has been transmitted through the cells S is transmitted through the observation window 53, is then deflected by the right-angle prism 55, and enters the stereo optical system 25.

According to the observation device 51 of this embodiment, during rotation of the stirring shaft 17a, when the observation window 53 is aligned with the incident position of the stereo optical system 25, images of views of the cells S are acquired. In this case, because the stereo optical system 25 is not rotated, the configuration can be made simple. Furthermore, the stereo optical system 25 is accommodated inside the stirring shaft 17a, thereby preventing the stereo optical system 25 from obstructing the flow of the culture fluid W and the cells S. In this embodiment, a 45° mirror may be adopted instead of the right-angle prism 55.

In this embodiment, the stereo optical system 25 may also be rotated about the stirring shaft 17a together with the stirring shaft 17a.

With this configuration, during rotation of the stirring shaft 17a, when the observation window 53 and the incident position of the stereo optical system 25 are opposed to the light source 21, images of views of the cells S are acquired. In this case, the stereo optical system 25 is rotated together with the stirring shaft 17a, thereby making it possible to make an image-acquisition area follow the flow of the culture fluid W and the cells S.

Figure 20:
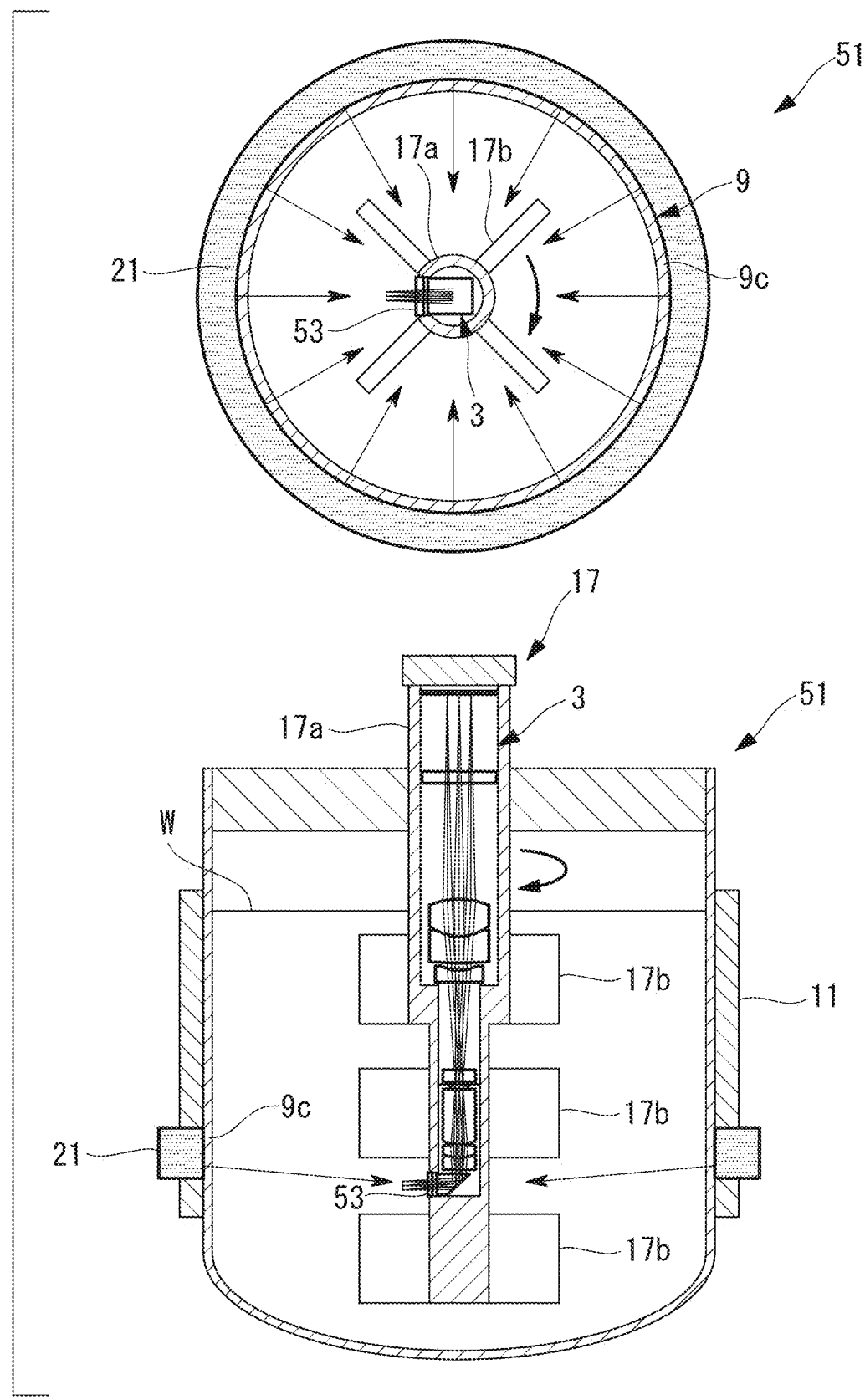
FIG. 20 is a view showing a transverse section and a longitudinal section of an observation device according to a modification of the fourth embodiment of the present invention.

Furthermore, in this embodiment, for example, as shown in FIG. 20, the light source 21 may emit illumination light from the entire circumferential area outside the culture vessel 9 toward the observation window 53. Furthermore, the stereo optical system 25 may be rotated about the stirring shaft 17a together with the stirring shaft 17a. In this case, the illumination window 9c is formed over the entire circumferential area of the culture vessel 9.

With this configuration, it is not necessary to align the timing at which illumination light is emitted from the light source 21 with the timing at which the observation window 53 and the incident position of the stereo optical system 25 are opposed to the light source 21, and image acquisition can be always performed.

Fifth Embodiment

Next, an observation device according to a fifth embodiment of the present invention will be described below with reference to the drawings.

Figure 21:
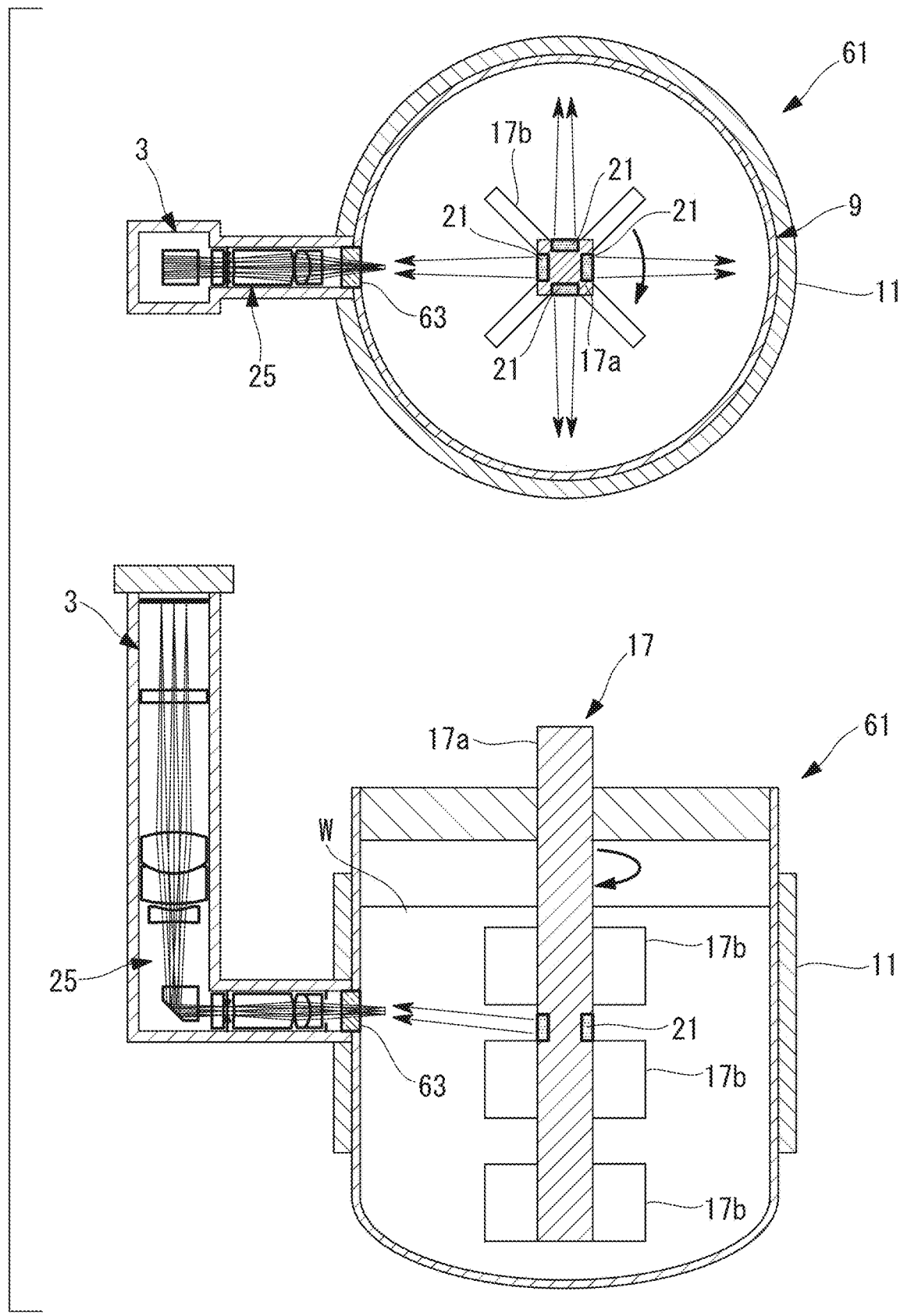
FIG. 21 is a view showing a transverse section and a longitudinal section of an observation device according to a fifth embodiment of the present invention.

As shown in FIG. 21, for example, an observation device 61 of this embodiment differs from that of the fourth embodiment in that the camera unit 3 is disposed outside the culture vessel 9.

In the description of this embodiment, identical reference signs are assigned to parts having configurations common to those of the observation device 51 of the above-described fourth embodiment, and a description thereof will be omitted.

As shown in FIG. 21, in the observation device 61 of this embodiment, the culture vessel 9 has, in a side surface thereof, a parallel-plate observation window 63 that is made of an optically transparent material.

The stereo optical system 25 is disposed outside the culture vessel 9 and images light from the cells S that has been transmitted through the observation window 63.

A plurality of light sources 21 are attached to the stirring shaft 17a, and illumination light is emitted from the respective light sources 21 toward radially outer sides of the stirring shaft 17a. The respective light sources 21 are disposed so as to be shifted in height from the observation window 63. Furthermore, the respective light sources 21 are rotated about the stirring shaft 17a together with the stirring shaft 17a. Accordingly, illumination light emitted from the light sources 21 is radiated on the cells S in the culture fluid W. Then, transmitted light of the illumination light that has been transmitted through the cells S is transmitted through the observation window 63 and enters the stereo optical system 25.

According to the observation device 61 of this embodiment, during rotation of the stirring shaft 17a, when any of the light sources 21 is opposed to the observation window 63, images of views of the cells S are acquired. In this case, because the stereo optical system 25 is not accommodated inside the stirring shaft 17a, it is possible to reduce the diameter of the stirring shaft 17a and to reduce the size of the culture vessel 9.

Furthermore, the stereo optical system 25 is disposed outside the culture vessel 9, thereby preventing the flow of the culture fluid W and the cells S in the culture vessel 9 from being obstructed by the stereo optical system 25. Furthermore, light from the cells S in the culture fluid W, the cells S being irradiated with illumination light, is transmitted through the parallel-plate observation window 63 and enters the stereo optical system 25, thereby making it possible to suppress the generation of aberrations. Furthermore, small light sources, such as LEDs, can be used as the light sources 21. Furthermore, the light sources 21 are disposed so as to be shifted in height from the observation window 53, thereby making it possible to obliquely illuminate the cells S.

This embodiment can be modified to the following configurations.

Figure 22:
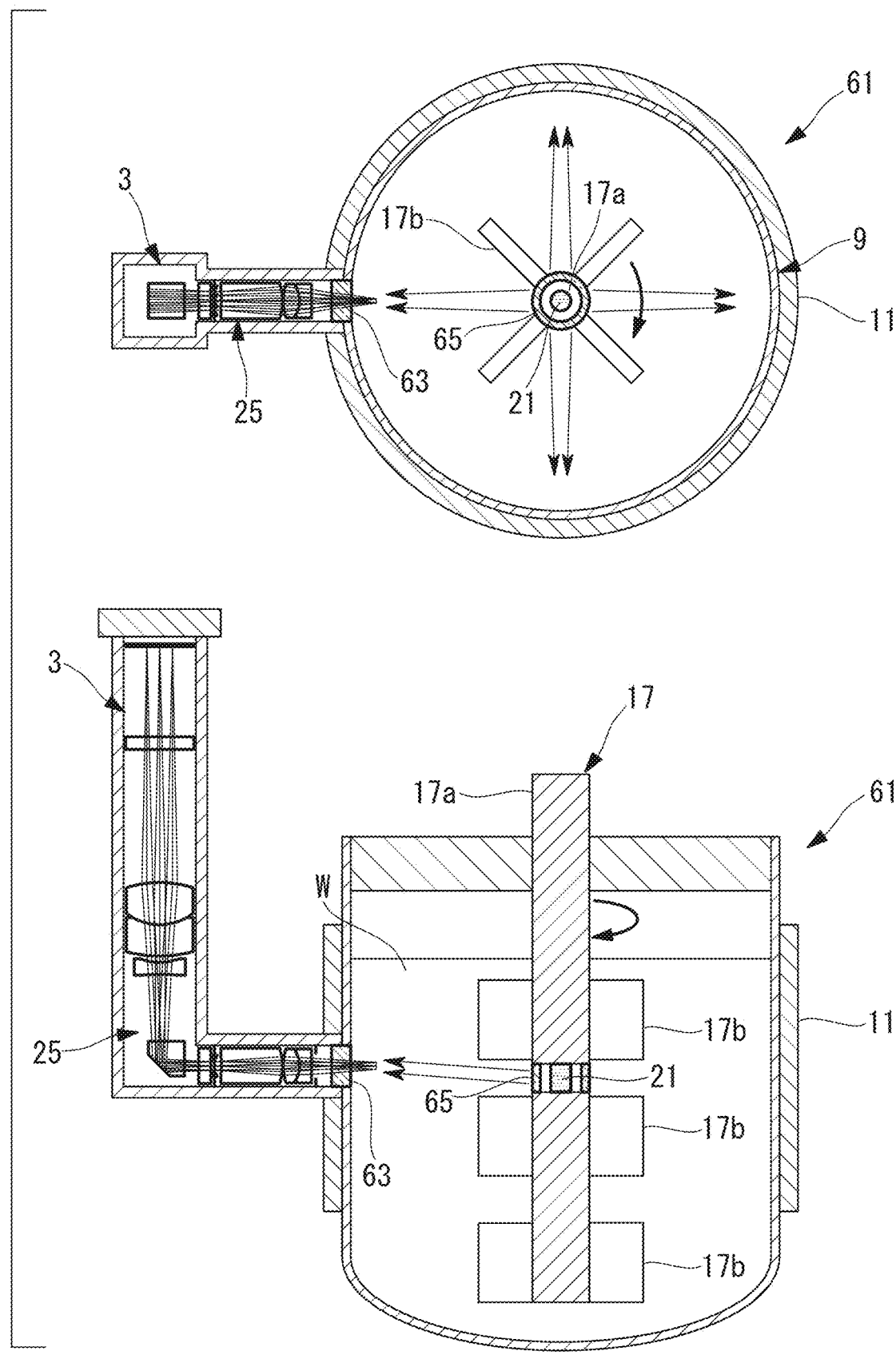
FIG. 22 is a view showing a transverse section and a longitudinal section of an observation device according to a first modification of the fifth embodiment of the present invention.

In a first modification, for example, as shown in FIG. 22, it is also possible to make the stirring shaft 17a hollow and to accommodate the light source 21 inside the stirring shaft 17a. Furthermore, while being rotated about the stirring shaft 17a together with the stirring shaft 17a, the light source 21 may emit illumination light from the entire circumference of the stirring shaft 17a toward radially outer sides of the stirring shaft 17a.

In this case, the stirring shaft 17a has a ring-shaped transmissive window 65 that surrounds the light source 21 and that is made of an optically transparent material. The transmissive window 65 may have a comparative diffusion function of imparting various angle components to illumination light transmitted therethrough.

According to this modification, illumination light emitted from the light source 21 and transmitted through the transmissive window 65 of the stirring shaft 17a is radiated onto the cells S in the culture fluid W. Then, transmitted light of the illumination light that has been transmitted through the cells S is transmitted through the observation window 63 and enters the stereo optical system 25. In this case, while being rotated together with the stirring shaft 17a, the light source 21 emits illumination light radially outward from the entire circumference of the stirring shaft 17a, thereby making it possible to always perform image acquisition by using the single light source 21.

Figure 23:
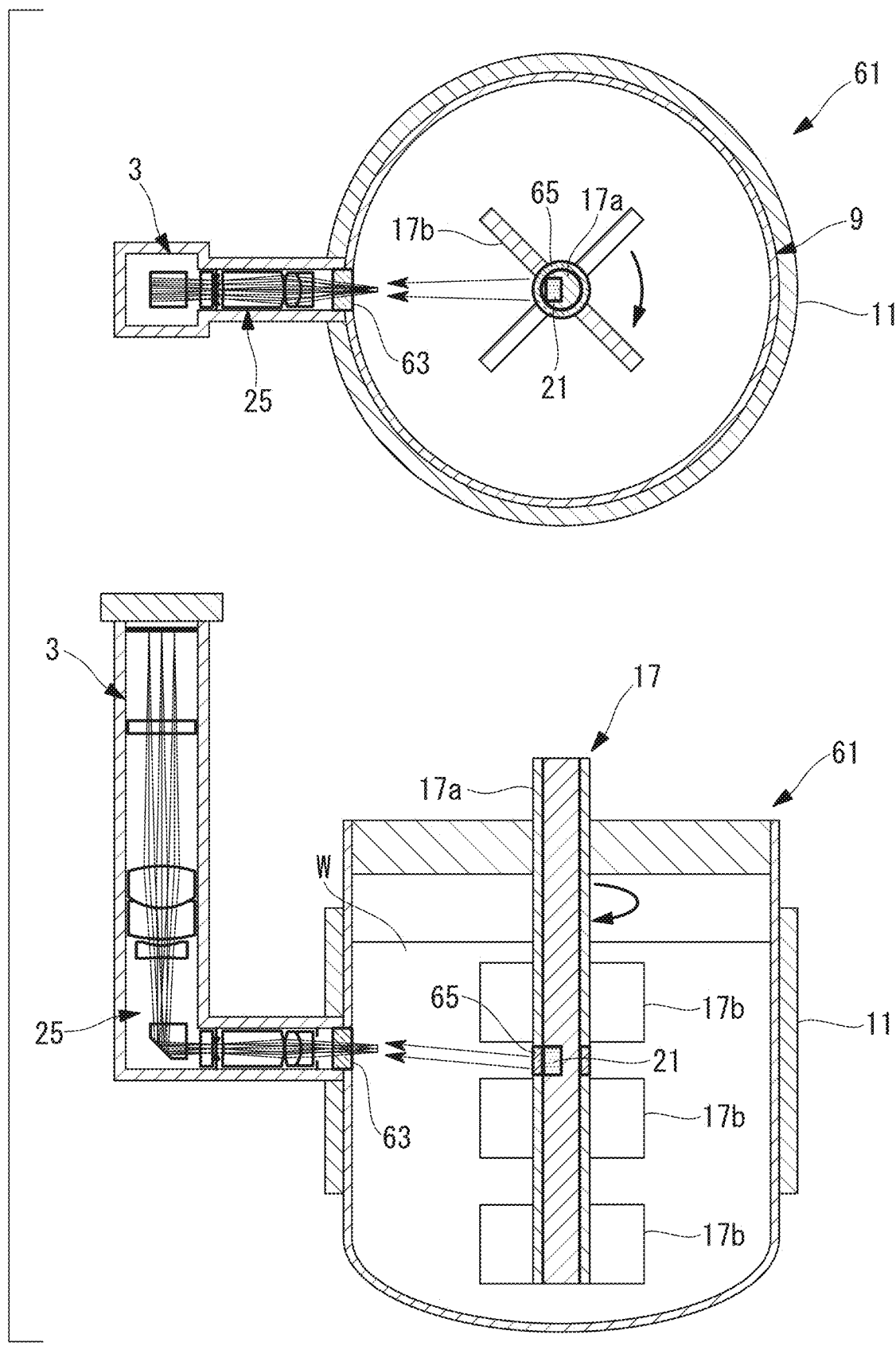
FIG. 23 is a view showing a transverse section and a longitudinal section of another observation device according to the first modification of the fifth embodiment of the present invention.

In this modification, although the light source 21 is rotated together with the stirring shaft 17a, instead of this, for example, as shown in FIG. 23, the light source 21 may emit illumination light toward the observation window 63 without being rotated about the stirring shaft 17a.

With this configuration, illumination light emitted from the light source 21 and transmitted through the transmissive window 65 of the stirring shaft 17a is radiated onto the cells S in the culture fluid W. Then, transmitted light of the illumination light that has been transmitted through the cells S is transmitted through the observation window 63 and enters the stereo optical system 25. In this case, because the light source 21 is not rotated, a circuit connected to the light source 21 does not become complicated.

In a second modification, for example, as shown in FIG. 24, the light source 21 may be disposed outside the culture vessel 9 and may emit illumination light toward the observation window 63. Furthermore, the light source 21 and the observation window 63 may be disposed so as to opposed to each other in a radial direction of the stirring shaft 17a, with the stirring shaft 17a sandwiched therebetween.

Furthermore, the culture vessel 9 may have the parallel-plate illumination window 9c, through which illumination light emitted from the light source 21 is transmitted. Furthermore, in the stirring shaft 17a, an area located in a light path of the illumination light may be formed of a light transmissive member 17c that is made of an optically transparent material.

With this configuration, illumination light emitted from the light source 21 and transmitted through the illumination window 9c is transmitted through the light transmissive member 17c of the stirring shaft 17a. Then, the illumination light is radiated onto the cells S in the culture fluid W, and transmitted light of the illumination light that has been transmitted through the cells S is transmitted through the observation window 63 and enters the stereo optical system 25. In this case, the light source 21 and the stereo optical system 25 are disposed outside the culture vessel 9, thereby preventing the light source 21 and the stereo optical system 25 from obstructing the flow of the culture fluid W and the cells S.

Figure 25:
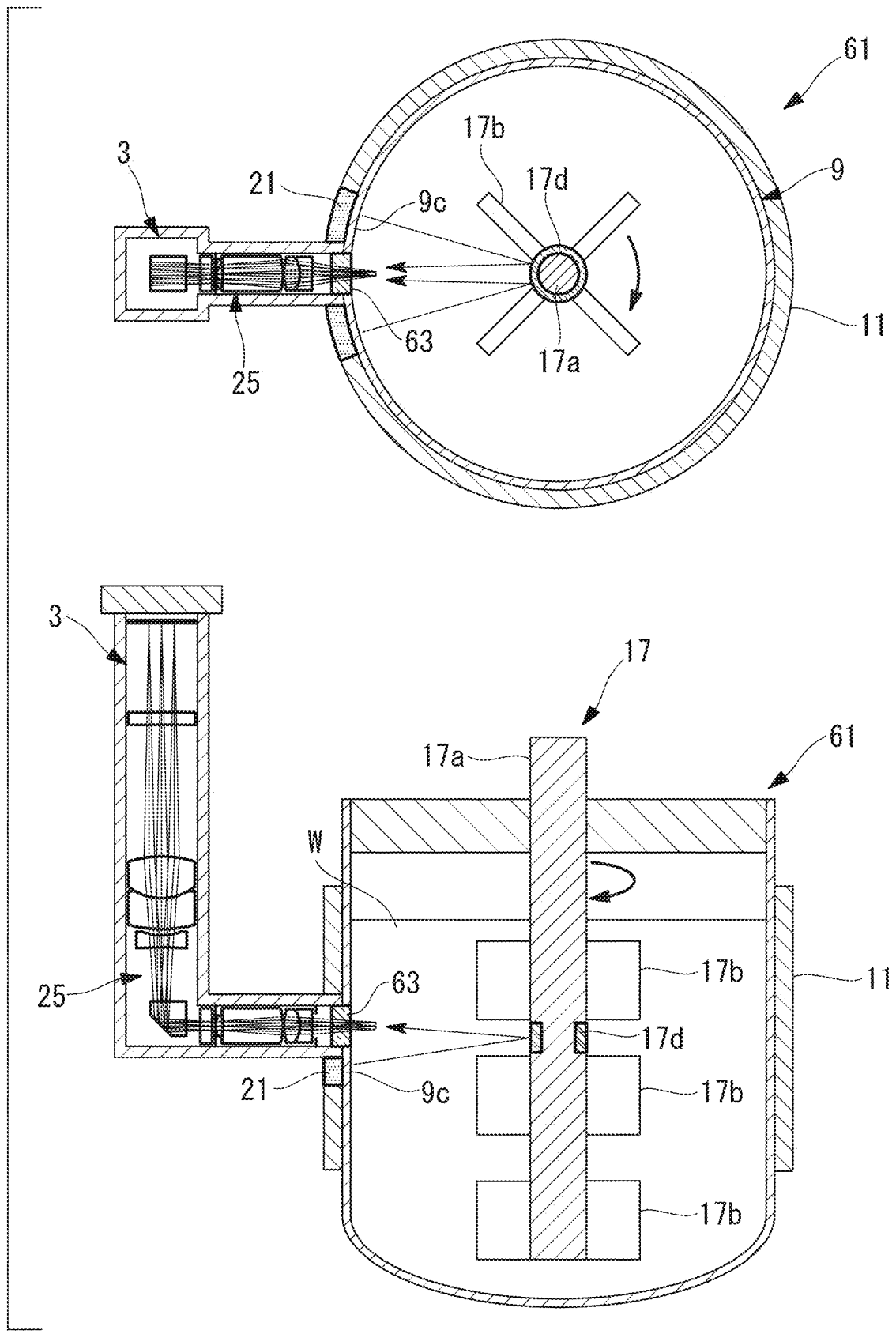
FIG. 25 is a view showing a transverse section and a longitudinal section of an observation device according to a third modification of the fifth embodiment of the present invention.

In a third modification, for example, as shown in FIG. 25, the light source 21 may be disposed outside the culture vessel 9 and may emit illumination light toward the stirring shaft 17a. Furthermore, the culture vessel 9 may have, in a side surface thereof, the parallel-plate illumination window 9c, through which illumination light emitted from the light source 21 is transmitted. Furthermore, in the stirring shaft 17a, an area located in a light path of the illumination light may be formed of a reflective member 17d that is made of a material reflecting the illumination light toward the observation window 63.

According to this modification, illumination light emitted from the light source 21 and transmitted through the illumination window 9c is reflected by the reflective member 17d of the stirring shaft 17a. Then, the illumination light is radiated onto the cells S in the culture fluid W, and transmitted light of the illumination light that has been transmitted through the cells S is transmitted through the observation window 63 and enters the stereo optical system 25.

In this case, the light source 21 and the stereo optical system 25 are disposed outside the culture vessel 9, thereby preventing the light source 21 and the stereo optical system 25 from obstructing the flow of the culture fluid W and the cells S. Furthermore, the light source 21 and the stereo optical system 25 can be disposed, outside the culture vessel 9, at positions close to each other, thus making it possible to save space.

Figure 26:
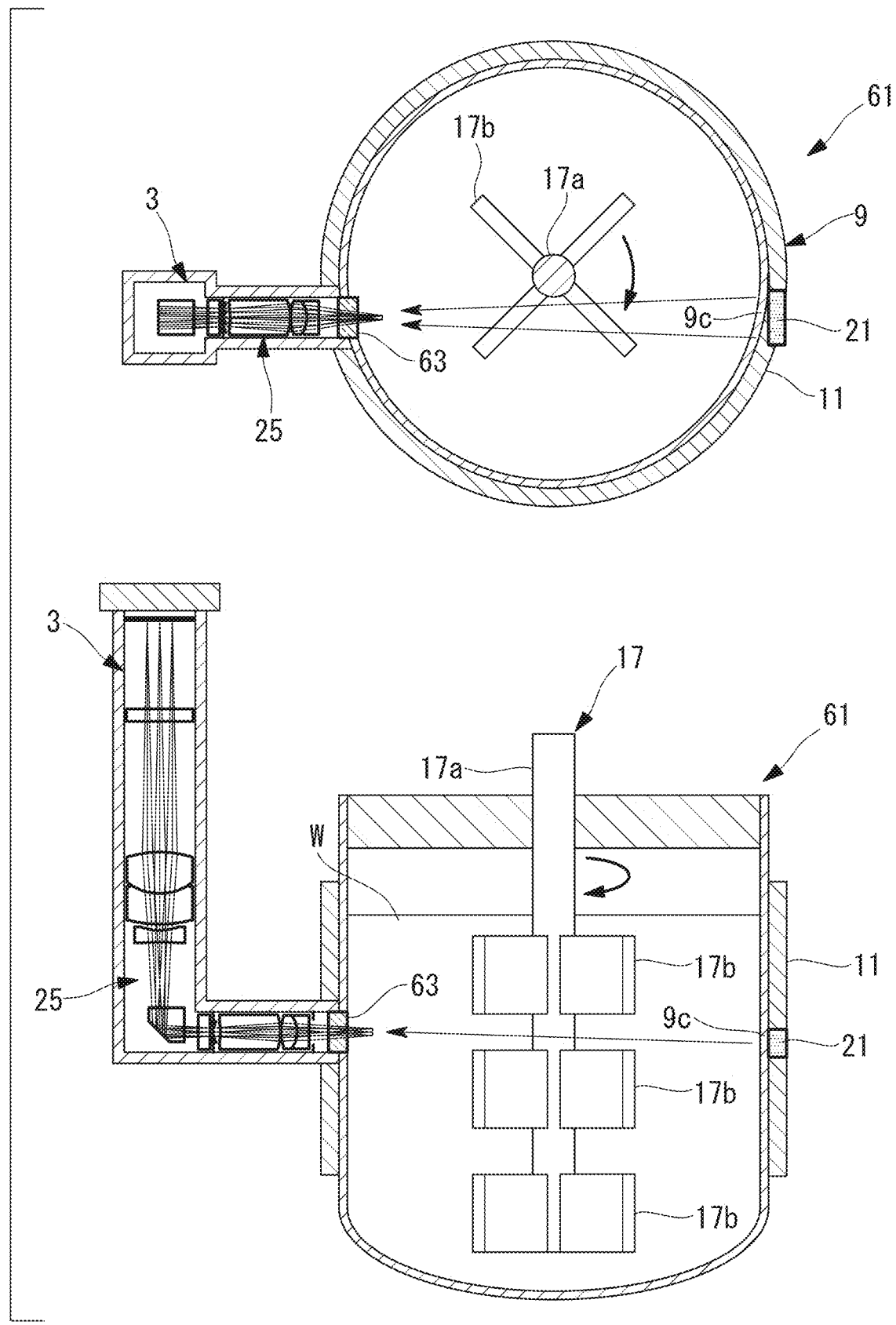
FIG. 26 is a view showing a transverse section and a longitudinal section of another observation device according to the second modification of the fifth embodiment of the present invention.

In the above-described second modification, for example, as shown in FIG. 26, the light source 21 and the illumination window 9c may be disposed so as to be opposed to the observation window 63, with their positions shifted in a radial direction of the stirring shaft 17a. Furthermore, illumination light emitted from the light source 21 may pass through a position shifted with respect to the stirring blades 17b in the longitudinal direction of the stirring shaft 17a and may enter the observation window 63.

With this configuration, illumination light emitted from the light source 21 and transmitted through the illumination window 9c is radiated onto the cells S in the culture fluid W without being blocked by the stirring shaft 17a and the stirring blades 17b. Then, transmitted light of the illumination light that has been transmitted through the cells S is transmitted through the observation window 63 and enters the stereo optical system 25. Therefore, except for the observation window 63 and the illumination window 9c, the configuration can be made simple as in conventional culture vessels.

Figure 27:
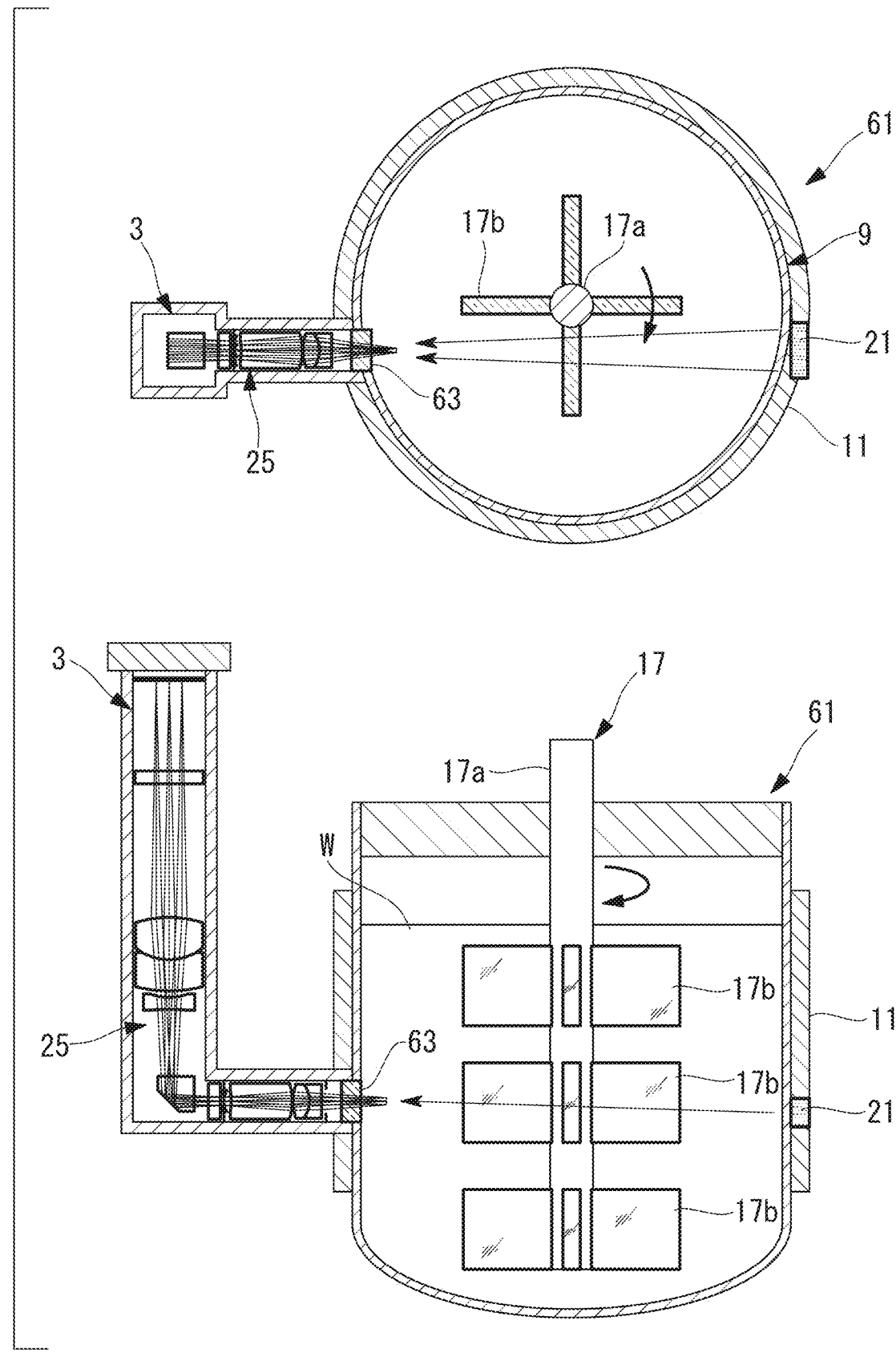
FIG. 27 is a view showing a transverse section and a longitudinal section of still another observation device according to the second modification of the fifth embodiment of the present invention.

In the example shown in FIG. 26, illumination light emitted from the light source 21 passes through a position shifted with respect to the stirring blades 17b in the longitudinal direction of the stirring shaft 17a. Instead of this, for example, as shown in FIG. 27, at least parts of the stirring blades 17b may be made of an optically transparent material, and illumination light emitted from the light source 21 may be transmitted through an area of the stirring blade 17b made of the optically transparent material.

With this configuration, illumination light emitted from the light source 21 and transmitted through the illumination window 9c is transmitted through the area of the stirring blade 17b made of the optically transparent material. Then, the illumination light is radiated onto the cells S in the culture fluid W, and transmitted light of the illumination light that has been transmitted through the cells S is transmitted through the observation window 63 and enters the stereo optical system 25. Therefore, inside the culture vessel 9, the cell density in an area corresponding to the depth where the stirring blade 17b is disposed can also be measured.

Figure 28:
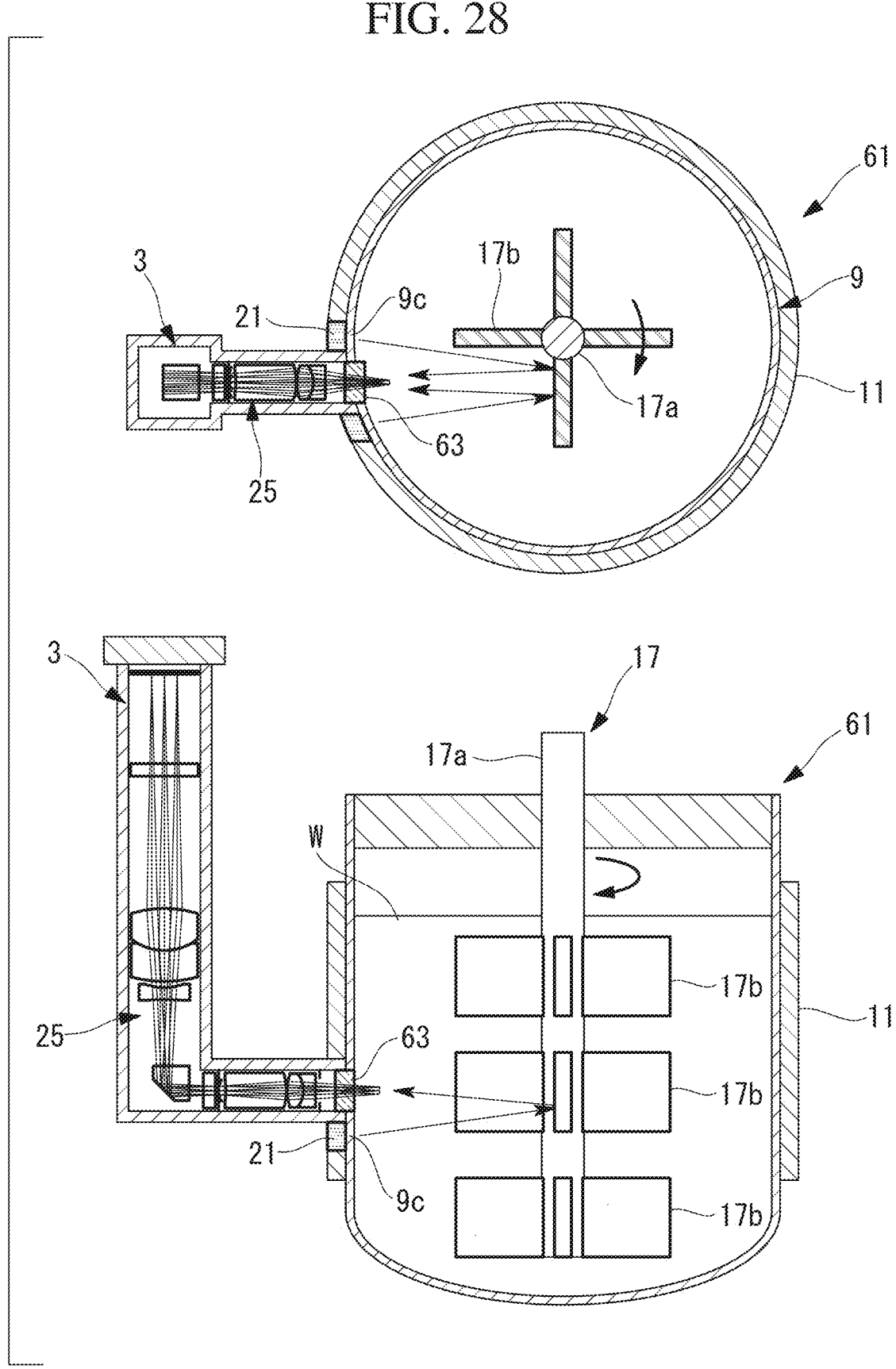
FIG. 28 is a view showing a transverse section and a longitudinal section of another observation device according to the third modification of the fifth embodiment of the present invention.

In the above-described third modification, for example, as shown in FIG. 28, the light source 21 may emit illumination light toward a corresponding one of the stirring blades 17b. Furthermore, in the stirring blade 17b, an area located in a light path of the illumination light may be made of a material that reflects the illumination light toward the observation window 63.

With this configuration, illumination light emitted from the light source 21 and transmitted through the illumination window 9c is reflected by the stirring blade 17b. Then, the illumination light is radiated onto the cells S in the culture fluid W, and transmitted light of the illumination light that has been transmitted through the cells S is transmitted through the observation window 63 and enters the stereo optical system 25.

In this case, the light source 21 and the stereo optical system 25 are disposed outside the culture vessel 9, thereby preventing the light source 21 and the stereo optical system 25 from obstructing the flow of the culture fluid W and the cells S. Furthermore, the light source 21 and the stereo optical system 25 can be disposed, outside the culture vessel 9, at positions close to each other, thus making it possible to save space.

Figure 29:
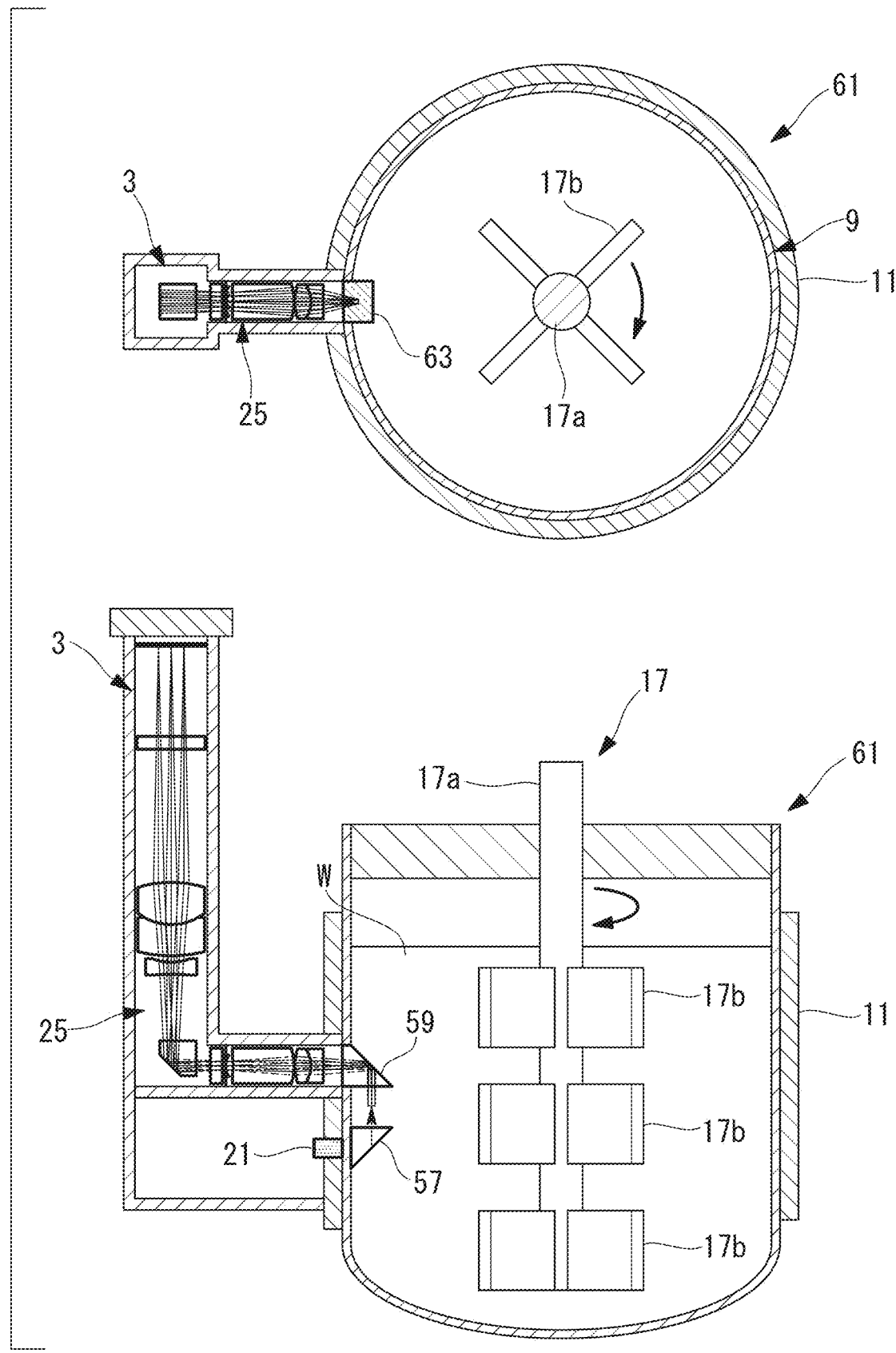
FIG. 29 is a view showing a transverse section and a longitudinal section of another observation device according to a fourth modification of the fifth embodiment of the present invention.

In a fourth modification, as shown in FIG. 29, the light source 21 may be disposed outside the culture vessel 9 and may emit illumination light toward the inside of the culture vessel 9. Furthermore, the culture vessel 9 may have, in a side surface thereof, a first prism 57 that deflects, in the culture vessel 9, illumination light emitted from the light source 21, in the direction along an inner circumferential surface of the culture vessel 9 and a second prism 59 that deflects, toward the outside of the culture vessel 9, transmitted light of the illumination light that has been deflected by the first prism 57 and then has been radiated onto the cells S in the culture fluid W. Then, the stereo optical system 25 may be disposed outside the culture vessel 9, and light emitted toward the outside of the culture vessel 9 by the second prism 59 may be imaged.

According to this modification, the flow of the culture fluid W and the cells S in the culture vessel 9 is prevented from being obstructed by the stereo optical system 25. In this case, light from the cells S is deflected by the second prism 59, thereby making it possible to allow the light from the cells S emitted in a direction intersecting the optical axis of the stereo optical system 25 to enter the stereo optical system 25. Furthermore, illumination light does not cross the inside of the culture vessel 9, thus making it possible to reduce the distance between the first prism 57 and the second prism 59. Accordingly, the volume of the culture fluid W in the light path of the illumination light is less, and the number of cells S therein is also less, thus making it possible to suppress the influence of scattering of illumination light and to acquire an image having high contrast.

Figure 30:
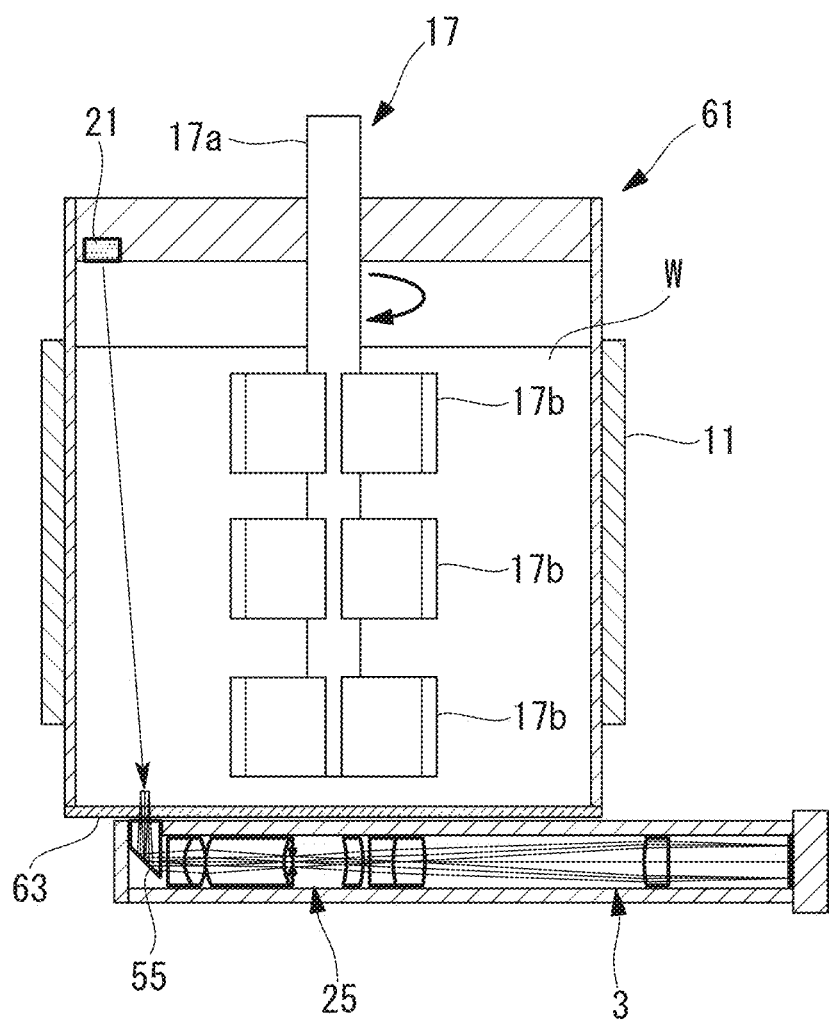
FIG. 30 is a view showing a longitudinal section of an observation device according to a fifth modification of the fifth embodiment of the present invention.

In a fifth modification, for example, as shown in FIG. 30, the culture vessel 9 may have the observation window 63 at a bottom surface thereof. Furthermore, the light source 21 may be disposed in the upper surface of the culture vessel 9 and may emit illumination light toward the observation window 63. Furthermore, the stereo optical system 25 may be disposed below the bottom surface of the culture vessel 9, and light from the cells S that has been transmitted through the observation window 63 and has been emitted to the outside of the culture vessel 9 may be imaged.

In this case, the stereo optical system 25 may be disposed along the bottom surface of the culture vessel 9. Furthermore, it is also possible to dispose, between the observation window 63 and the stereo optical system 25, the right-angle prism 55 that deflects light that has been transmitted through the observation window 63, in the direction along the bottom surface of the culture vessel 9, thereby allowing the light to enter the stereo optical system 25.

With this configuration, the flow of the culture fluid W and the cells S in the culture vessel 9 is prevented from being obstructed by the stereo optical system 25. Furthermore, the shape of the culture vessel 9 can be made simple.

The above-described fourth and fifth embodiments show example cases in which the observation window 63 of the stereo optical system 25 and the light source 21 are disposed such that the heights of the positions thereof are made different. Illumination light enters the stereo optical system 25 obliquely with respect to the optical axis of the stereo optical system 25, thereby making it possible to acquire an oblique-illumination image; thus, the light source 21 may be disposed so as to be shifted with respect to the optical axis of the stereo optical system 25. For example, the stereo optical system 25 may be disposed so as to be inclined with respect to the optical axis of illumination light emitted from the light source 21.

Sixth Embodiment

Next, a bag culture device (observation device) according to a sixth embodiment of the present invention will be described below with reference to the drawings.

Figure 31:
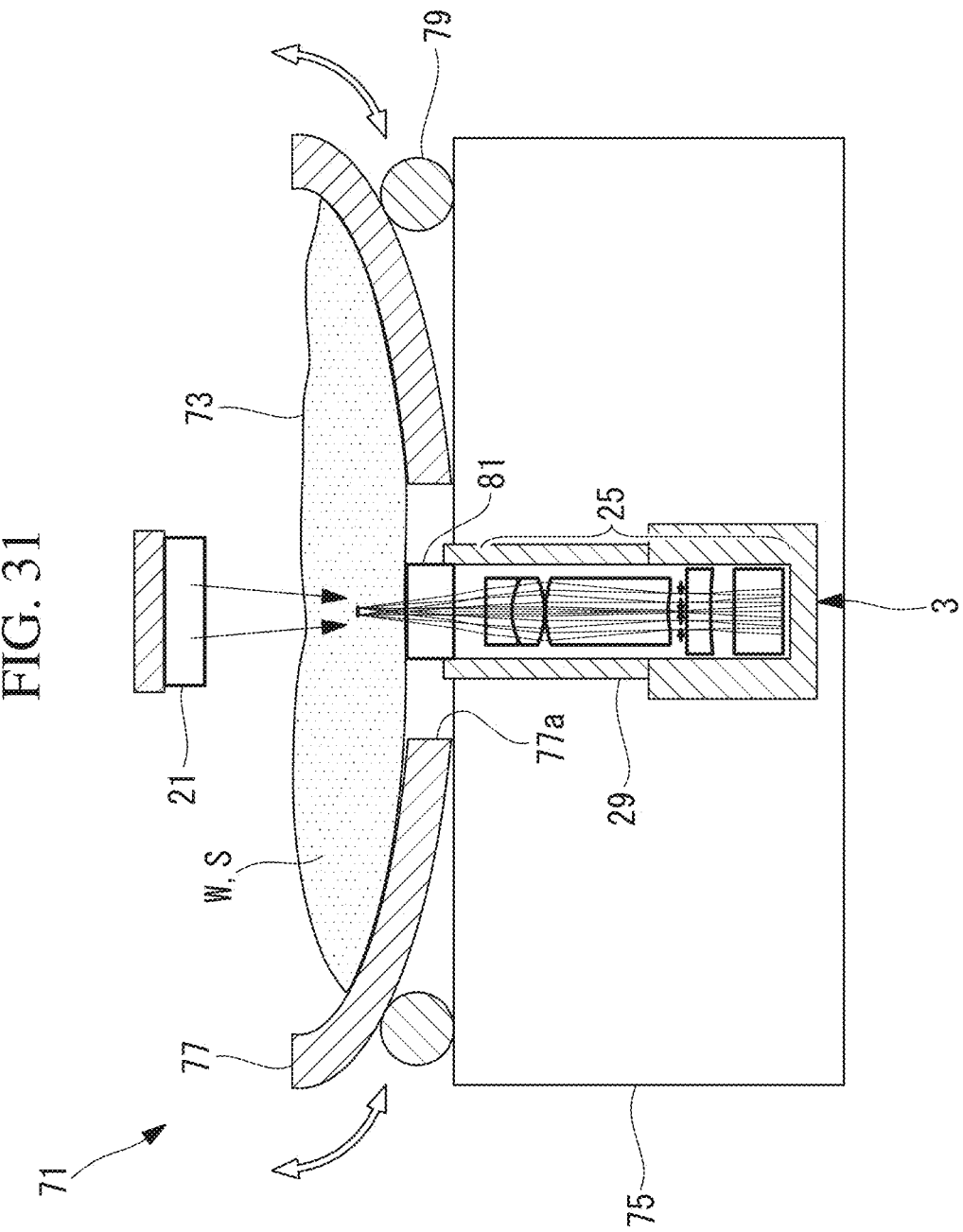
FIG. 31 is a longitudinal sectional view of a bag culture device according to a sixth embodiment of the present invention.
Figure 32:
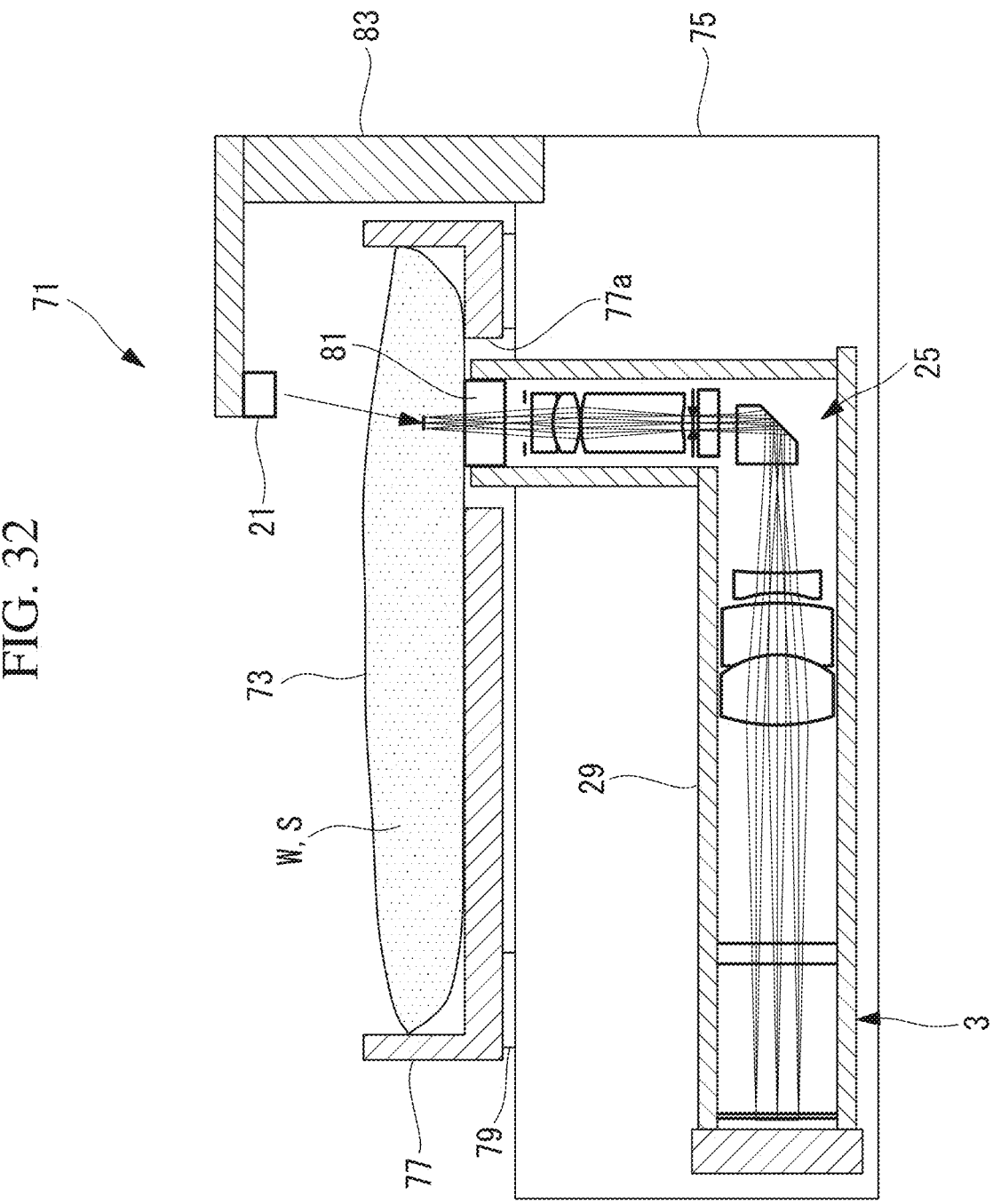
FIG. 32 is another longitudinal sectional view of the bag culture device shown in FIG. 31.

As shown in FIGS. 31 and 32, for example, a bag culture device 71 of this embodiment differs from the first to fifth embodiments in that the bag culture device 71 is used to observe cells S that are cultured while being accommodated inside a bag-shaped culture bag (culture vessel) 73 together with the culture fluid W.

In the description of this embodiment, identical reference signs are assigned to parts having configurations common to those of the observation devices 1, 51, and 61 of the above-described first to fifth embodiments, and a description thereof will be omitted.

The bag culture device 71 includes: a box-like casing part 75 that accommodates the camera unit 3; a placement part 77 that is mounted on the casing part 75 and on which the culture bag 73 is placed; and an oscillation mechanism 79 that makes the placement part 77 oscillate with respect to the casing part 75.

The camera unit 3 does not include the light source 21 and the light guide fiber 23 and is accommodated inside the casing part 75 without the distal-end unit 5 being mounted thereon. Furthermore, the camera unit 3 includes a parallel-plate observation window 81 that is made of an optically transparent material and that is disposed in front of the stereo optical system 25. In the camera unit 3, the observation window 81 is made to protrude from an upper surface of the casing part 75, and light that is transmitted through the observation window 81 and that enters the casing 29 is imaged by the stereo optical system 25.

The placement part 77 is installed on the upper surface of the casing part 75. The placement part 77 has a hole 77a through which the observation window 81 of the stereo optical system 25 is inserted. The hole 77a has a sufficient size to avoid interference of the placement part 77 with the observation window 81.

The casing part 75 has a light-source support part 83 that supports the light source 21. The light-source support part 83 disposes the light source 21 at a position above the culture bag 73, which is placed on the placement part 77, and holds the light source 21 so as to be oriented toward the observation window 81. The light source 21 is disposed, by the light-source support part 83, at a position shifted from the optical axis of the stereo optical system 25 in a direction intersecting the optical axis. The light source 21 radiates illumination light from obliquely above toward the observation window 81. Accordingly, it is possible to illuminate the cells S inside the culture bag 73 through oblique illumination and to acquire an image in which the contrast of the cells S has been improved.

The oscillation mechanism 79 is disposed between the upper surface of the casing part 75 and a lower surface of the placement part 77. The oscillation mechanism 79 makes the placement part 77 oscillate, with respect to the light source 21 and the stereo optical system 25, in a direction intersecting the optical axis of the stereo optical system 25. The oscillation mechanism 79 makes the culture bag 73 oscillate, thereby making it possible to stir the cells S inside the culture bag 73.

According to this embodiment, the culture bag 73, inside which the culture fluid W and the cells S are accommodated, is placed on the placement part 77, and the oscillation mechanism 79 makes the placement part 77 oscillate, thereby culturing the cells S while stirring the culture fluid W inside the culture bag 73.

In this state, illumination light emitted from the light source 21 is radiated onto the cells S inside the culture bag 73. Transmitted light of the illumination light that has been transmitted through the cells S is transmitted through the observation window 81, enters the stereo optical system 25, and is subjected to image acquisition by the image-acquisition device 27. In the bag culture device 71 of this embodiment, because a plurality of images in which the position of the same cell S is shifted according to the distance from the stereo optical system 25 are acquired, the cell density in the culture fluid W can be accurately calculated by the image analysis unit 7. Therefore, the cell density in the culture fluid W can be accurately measured regardless of the shape and size of the culture bag 73 to be used.

This embodiment can be modified to the following configurations.

Figure 33:
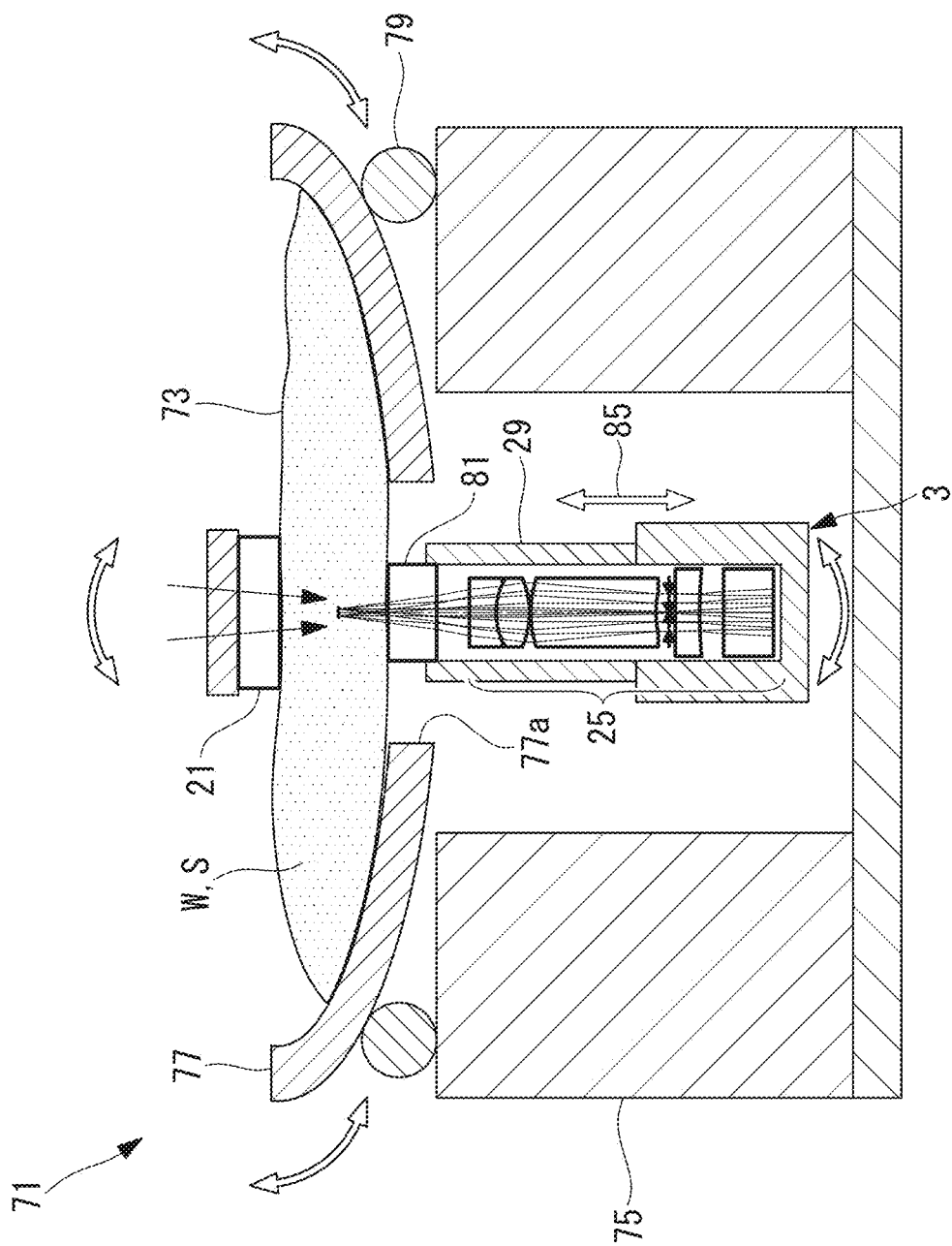
FIG. 33 is a longitudinal sectional view of a bag culture device according to a modification of the sixth embodiment of the present invention.
Figure 34:
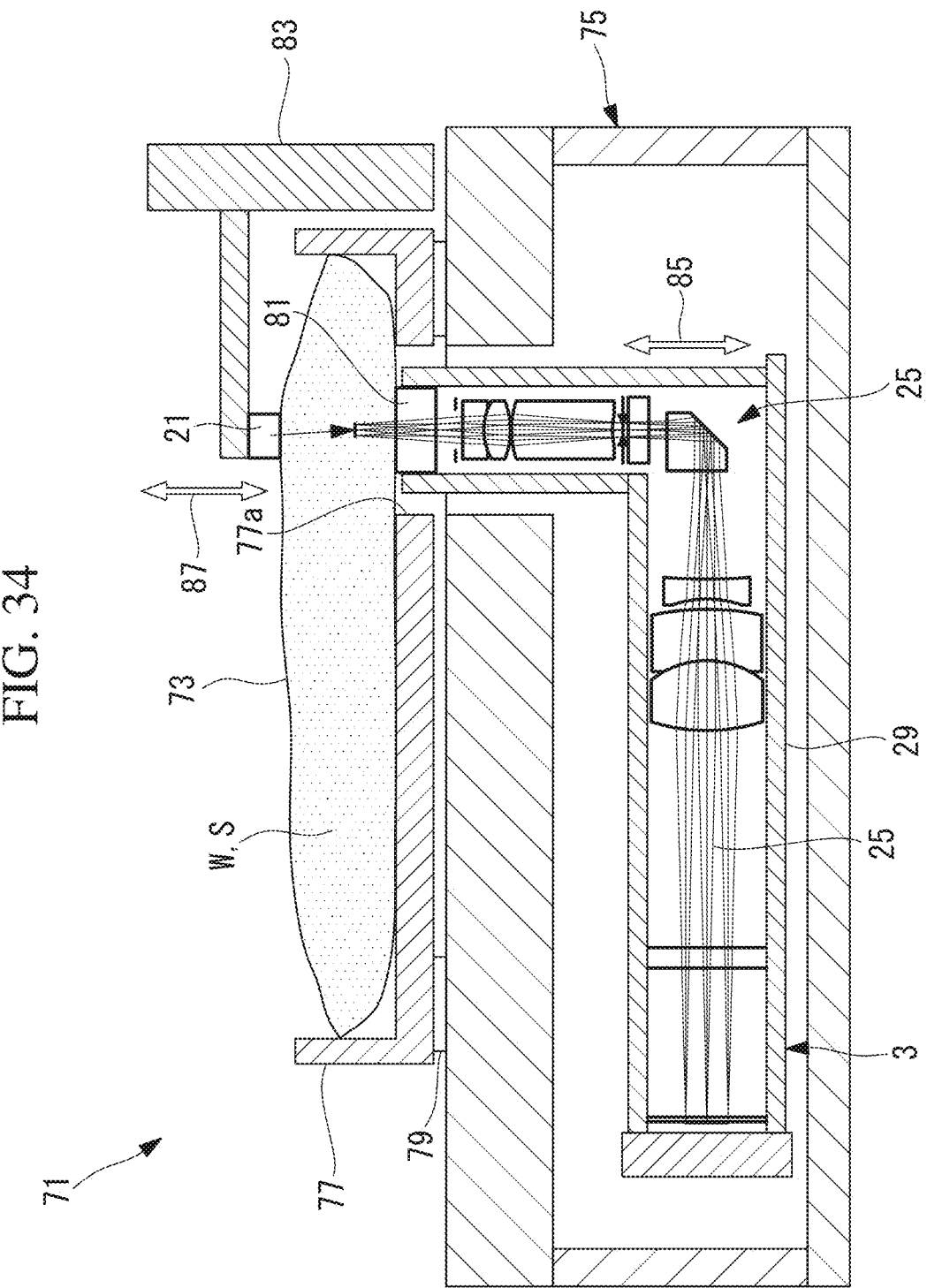
FIG. 34 is another longitudinal sectional view of the bag culture device shown in FIG. 33.

In this embodiment, the culture bag 73 on the placement part 77 is made to oscillate with respect to the light source 21 and the stereo optical system 25. Instead of this, for example, as shown in FIGS. 33 and 34, the oscillation mechanism 79 may make the light source 21 and the stereo optical system 25 oscillate together with the culture bag 73 on the placement part 77.

In this case, the respective distal ends of the light source 21 and the stereo optical system 25 may be placed in close contact with the culture bag 73 on the placement part 77. The light source 21 and the observation window 81 of the stereo optical system 25 are placed in close contact with the culture bag 73, thereby making it possible to further stabilize a state in which the cell density is measured. For example, in order to place the observation window 81 of the stereo optical system 25 in close contact with the culture bag 73, it is also possible to include a stereo-optical-system-position adjustment mechanism 85 that brings the stereo optical system 25, including the entire camera unit 3, close to and away from the culture bag 73 on the placement part 77. Furthermore, in order to place the light source 21 in close contact with the culture bag 73, the light-source support part 83 may include a light-source-position adjustment mechanism 87 that brings the light source 21 close to and away from the culture bag 73 on the placement part 77.

Figure 35:
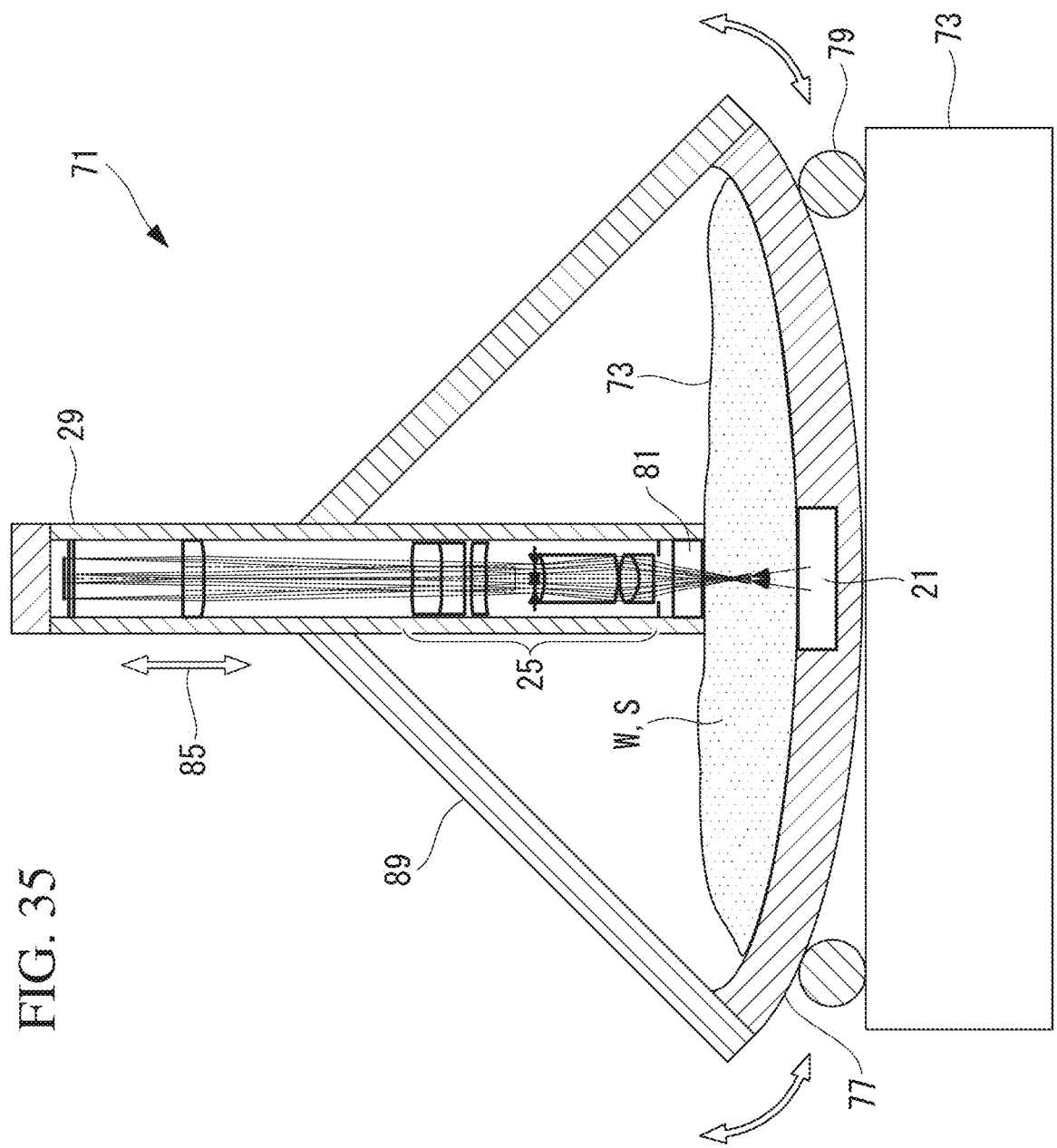
FIG. 35 is a longitudinal sectional view of a bag culture device according to another modification of the sixth embodiment of the present invention.

In this embodiment, the stereo optical system 25 is disposed below the culture bag 73, and the light source 21 is disposed above the culture bag 73. Instead of this, for example, as shown in FIG. 35, it is also possible to dispose the stereo optical system 25 above the culture bag 73 and to dispose the light source 21 below the culture bag 73. In FIG. 35, reference sign 89 denotes a camera-unit support part that supports the camera unit 3.

In this case, the light source 21 may be disposed on the placement part 77, and the light source 21 may radiate, from below, illumination light onto the culture bag 73 placed on the placement part 77. Furthermore, it is also possible to dispose the camera unit 3 above the placement part 77 and to radiate illumination light from the light source 21, thus making transmitted light that has been transmitted upward through the cells S in the culture bag 73 enter the stereo optical system 25.

Furthermore, in a state in which the light source 21 and the stereo optical system 25 are fixed, the oscillation mechanism 79 may make the culture bag 73 on the placement part 77 oscillate. Alternatively, the oscillation mechanism 79 may make the light source 21 and the stereo optical system 25 oscillate together with the culture bag 73 on the placement part 77. In this case, it is also possible to adopt the stereo-optical-system-position adjustment mechanism 85, which brings the observation window 81 of the stereo optical system 25 into close contact with the culture bag 73 on the placement part 77.

Although the embodiments of the present invention have been described in detail above with reference to the drawings, specific configurations are not limited to these embodiments, and design changes etc. that do not depart from the scope of the present invention are also encompassed. For example, the present invention is not limited to the above-described embodiments and modifications and can be applied to an embodiment obtained by appropriately combining these embodiments and modifications, without particular limitation.

The above-described embodiment also leads to the following aspects.

According to one aspect, the present invention provides an observation device including: a stereo image-acquisition optical system that acquires images of cells floating in a culture fluid inside a culture vessel; and an image analysis unit that calculates a cell density of the cells on the basis of the images acquired by the stereo image-acquisition optical system.

According to this aspect, the stereo image-acquisition optical system acquires a plurality of images in which the position of the same cell is shifted in accordance with the distance from the stereo image-acquisition optical system. Therefore, because the three-dimensional position of each cell is found on the basis of these images, the image analysis unit can accurately calculate the cell density in a culture fluid. In the observation device according to the above-described aspect, the stereo image-acquisition optical system may include a stereo optical system that forms, for the same cell floating in the culture fluid, two views with parallax due to being viewed from different viewpoints, and an image-acquisition device that acquires images of the two views formed by the stereo optical system; and the image analysis unit may identify the positions of the cells included in the respective images of the two views, the images being acquired by the image-acquisition device, and may calculate the cell density on the basis of the number of cells present within a predetermined region.

The stereo optical system forms, for the same cell in the culture fluid, two views with parallax due to being viewed from different viewpoints, thereby shifting the position of the same cell between images of the two views, the images being acquired by the image-acquisition device, in accordance with the distance from the stereo optical system.

Specifically, the shift amount between images becomes smaller as the distance of a cell from the stereo optical system becomes closer, and the shift amount between images becomes larger as the distance of a cell therefrom becomes farther.

Therefore, because the three-dimensional position of each cell is found, the image analysis unit can accurately distinguish between cells that are included in the predetermined region and cells that are not included therein and can calculate the cell density in the culture fluid. Thus, it is possible to accurately measure the cell density in the culture fluid during suspension culturing, regardless of the shape, the size, etc. of the culture vessel to be used.

In the observation device according to the above-described aspect, the stereo optical system may include: an objective optical system that focuses light from the cells; an aperture opening part that splits the light focused by the objective optical system; and a prism that deflects light rays obtained after the splitting at the aperture opening part.

In the observation device according to the above-described aspect, the stereo optical system may include: an objective optical system that focuses light from the cells; an aperture opening part that splits the light focused by the objective optical system; and an imaging optical system that separately images light rays obtained after the splitting at the aperture opening part.

In the observation device according to the above-described aspect, the stereo optical system may include a prism that focuses light from the cells, thereby splitting the light into the two views.

The observation device according to the above-described aspect may further include an oblique illumination part that radiates illumination light onto the cells at an angle in a direction intersecting an arrangement direction of the viewpoints of the stereo optical system.

With this configuration, because the refractive indexes are different in the culture fluid and inside the cell, light is bent at the boundary between the culture fluid and the cell. In this case, a region corresponding to light that is bent in such a direction as to pass through the outside of the pupil becomes dark in an image plane, and a region corresponding to light that is bent in such a direction as to pass through the inside of the pupil becomes bright in the image plane. Therefore, it is possible to acquire an image in which the contrast of the cells has been improved.

In the observation device according to the above-described aspect, the culture vessel may have, in a side surface thereof, a parallel-plate observation window that is made of an optically transparent material, and the stereo optical system may be disposed outside the culture vessel and may image light that is transmitted from the cells through the observation window and is emitted toward the outside of the culture vessel.

With this configuration, the flow of the culture fluid and the cells in the culture vessel is prevented from being obstructed by the stereo optical system. In this case, light from the cells is transmitted through the parallel-plate observation window and is made to enter the stereo optical system, thereby making it possible to suppress the generation of aberrations.

In the observation device according to the above-described aspect, the culture vessel may have, in a side surface thereof, a prism that deflects light from the cells to emit the light toward an outside of the culture vessel, and the stereo optical system may be disposed outside the culture vessel and may image the light emitted by the prism toward the outside of the culture vessel.

With this configuration, the flow of the culture fluid and the cells in the culture vessel is prevented from being obstructed by the stereo optical system. In this case, light from the cells is deflected by the prism, thereby making it possible to allow the light from the cells emitted from a direction intersecting the optical axis of the stereo optical system to enter the stereo optical system.

The observation device according to the above-described aspect may further include a stirring mechanism that includes a hollow stirring shaft extending inside the culture vessel in a depth direction of the culture vessel and a stirring blade rotated about the stirring shaft and that stirs the culture fluid when the stirring blade is rotated about the stirring shaft, wherein the stirring shaft may have a parallel-plate observation window that is made of an optically transparent material; and the stereo optical system may be accommodated inside the stirring shaft and may image light from the cells that is transmitted through the observation window and that enters the stirring shaft.

With this configuration, the stereo optical system can be disposed inside the culture vessel by using a space inside the stirring shaft of the stirring mechanism.

The observation device according to the above-described aspect may further include a light source that emits illumination light toward the observation window from a radially outer side of the stirring shaft, wherein the stereo optical system may not be rotated about the stirring shaft.

With this configuration, image acquisition is performed when the observation window is aligned with the incident position of the stereo optical system during rotation of the stirring shaft. In this case, because the stereo optical system is not rotated, the configuration can be made simple. Furthermore, the stereo optical system is accommodated inside the stirring shaft, thereby preventing the stereo optical system from obstructing the flow of the culture fluid and the cells.

The observation device according to the above-described aspect may further include a light source that emits illumination light toward the observation window from a radially outer side of the stirring shaft, wherein the stereo optical system may be rotated about the stirring shaft together with the stirring shaft.

With this configuration, image acquisition is performed when the observation window and the incident position of the stereo optical system are opposed to the light source during rotation of the stirring shaft. In this case, the stereo optical system is rotated together with the stirring shaft, thereby making it possible to make an image-acquisition area follow the flow of the culture fluid and the cells.

The observation device according to the above-described aspect may further include a light source that emits illumination light toward the observation window from an entire circumferential area at a radially outer side of the stirring shaft, wherein the stereo optical system may be rotated about the stirring shaft together with the stirring shaft.

With this configuration, it is not necessary to align the timing at which illumination light is emitted from the light source with the timing at which the observation window and the incident position of the stereo optical system are opposed to the light source, and image acquisition can be always performed.

The observation device according to the above-described aspect may further include: a stirring mechanism that includes a stirring shaft extending inside the culture vessel in a depth direction of the culture vessel and a stirring blade rotated about the stirring shaft and that stirs the culture fluid when the stirring blade is rotated about the stirring shaft; and a plurality of light sources that are provided on the stirring shaft so as to be capable of being rotated together with the stirring shaft and that emit illumination light toward radially outer sides of the stirring shaft, wherein the plurality of light sources may be arranged in a circumferential direction of the stirring shaft.

With this configuration, image acquisition is performed when any of the light sources is opposed to the observation window during rotation of the stirring shaft. In this case, because the stereo optical system is not accommodated inside the stirring shaft, it is possible to reduce the diameter of the stirring shaft.

The observation device according to the above-described aspect may further include: a stirring mechanism that includes a hollow stirring shaft extending inside the culture vessel in a depth direction of the culture vessel and a stirring blade rotated about the stirring shaft and that stirs the culture fluid when the stirring blade is rotated about the stirring shaft; and a light source that is accommodated inside the stirring shaft and that emits illumination light radially outward from an entire circumference of the stirring shaft while being rotated together with the stirring shaft, wherein the stirring shaft may have a ring-shaped transmissive window that is made of an optically transparent material and that surrounds the light source.

With this configuration, illumination light emitted from the light source and transmitted through the transmissive window of the stirring shaft is radiated onto the cells in the culture fluid. Then, transmitted light of the illumination light that has been transmitted through the cells is transmitted through the observation window of the culture vessel and enters the stereo optical system. In this case, while being rotated about the stirring shaft together with the stirring shaft, the light source emits illumination light radially outward from the entire circumference of the stirring shaft, thereby making it possible to always perform image acquisition with the single light source.

The observation device according to the above-described aspect may further include: a stirring mechanism that includes a hollow stirring shaft extending inside the culture vessel in a depth direction of the culture vessel and a stirring blade rotated about the stirring shaft and that stirs the culture fluid when the stirring blade is rotated about the stirring shaft; and a light source that is accommodated inside the stirring shaft of the stirring mechanism and that emits illumination light toward the observation window, wherein the stirring shaft may have a ring-shaped transmissive window that is made of an optically transparent material and that surrounds the light source; and the light source may not be rotated about the stirring shaft.

With this configuration, illumination light emitted from the light source is transmitted through the transmissive window of the stirring shaft, passes through the culture fluid inside the culture vessel, is then transmitted through the observation window of the culture vessel, and enters the stereo optical system. In this case, because the light source is not rotated, a circuit connected to the light source is prevented from being complicated.

The observation device according to the above-described aspect may further include: a stirring mechanism that includes a stirring shaft extending inside the culture vessel in a depth direction of the culture vessel and a stirring blade rotated about the stirring shaft and that stirs the culture fluid when the stirring blade is rotated about the stirring shaft; and a light source that is disposed outside the culture vessel so as to be opposed to the observation window in a radial direction of the stirring shaft, with the stirring shaft sandwiched therebetween, and that emits illumination light toward the observation window, wherein the culture vessel may have, in the side surface, a parallel-plate illumination window through which the illumination light emitted from the light source is transmitted; and an area, of the stirring shaft, located in a light path of the illumination light may be made of an optically transparent material.

With this configuration, illumination light emitted from the light source and transmitted through the illumination window is transmitted through the optically transparent area of the stirring shaft inside the culture vessel, is then transmitted through the observation window disposed so as to opposed to the light source in a radial direction of the stirring shaft, and enters the stereo optical system. In this case, the light source and the stereo optical system are disposed outside the culture vessel, thereby preventing the light source and the stereo optical system from obstructing the flow of the culture fluid and the cells.

The observation device according to the above-described aspect may further include: a stirring mechanism that includes a stirring shaft extending inside the culture vessel in a depth direction of the culture vessel and a stirring blade rotated about the stirring shaft and that stirs the culture fluid inside the culture vessel when the stirring blade is rotated about the stirring shaft; and a light source that is disposed outside the culture vessel and that emits illumination light toward the stirring shaft, wherein the culture vessel may have, in the side surface thereof, a parallel-plate illumination window through which the illumination light emitted from the light source is transmitted; and an area, of the stirring shaft, located in a light path of the illumination light may be made of a material that reflects the illumination light toward the observation window.

With this configuration, illumination light emitted from the light source and transmitted through the illumination window is reflected at the reflective area of the stirring shaft inside the culture vessel, is then transmitted through the observation window, and enters the stereo optical system. In this case, the light source and the stereo optical system are disposed outside the culture vessel, thereby preventing the light source and the stereo optical system from obstructing the flow of the culture fluid and the cells. Furthermore, the light source and the stereo optical system can be disposed, outside the culture vessel, at positions close to each other, thus making it possible to save space.

The observation device according to the above-described aspect may further include: a stirring mechanism that includes a stirring shaft extending inside the culture vessel in a depth direction of the culture vessel and a stirring blade rotated about the stirring shaft and that stirs the culture fluid when the stirring blade is rotated about the stirring shaft; and a light source that is disposed outside the culture vessel so as to be opposed to the observation window at a position shifted in a radial direction of the stirring shaft, with the stirring mechanism sandwiched therebetween, and that emits illumination light toward the observation window, wherein the culture vessel may have, in the side surface thereof, a parallel-plate illumination window through which the illumination light emitted from the light source is transmitted; and the illumination light emitted from the light source may pass through a position shifted in a longitudinal direction of the stirring shaft with respect to the stirring blade and may enter the observation window.

With this configuration, illumination light emitted from the light source and transmitted through the illumination window passes through the culture vessel without being blocked by the stirring shaft and the stirring blade, is then transmitted through the observation window, and enters the stereo optical system. Therefore, except for the observation window and the illumination window, the configuration can be made simple as in conventional culture vessels.

The observation device according to the above-described aspect may further include: a stirring mechanism that includes a stirring shaft extending inside the culture vessel in a depth direction of the culture vessel and a stirring blade rotated about the stirring shaft and that stirs the culture fluid when the stirring blade is rotated about the stirring shaft; and a light source that is disposed outside the culture vessel so as to be opposed to the observation window at a position shifted in a radial direction of the stirring shaft, with the stirring mechanism sandwiched therebetween, and that emits illumination light toward the observation window, wherein the culture vessel may have a parallel-plate illumination window through which the illumination light emitted from the light source is transmitted; at least part of the stirring blade may be made of an optically transparent material; and the illumination light emitted from the light source may be transmitted through an area, of the stirring blade, made of the optically transparent material, and may enter the observation window.

With this configuration, illumination light emitted from the light source and transmitted through the illumination window is transmitted through the optically transparent area of the stirring blade, is then transmitted through the observation window, and enters the stereo optical system. Therefore, inside the culture vessel, the cell density in the area corresponding to the depth where the stirring blade is disposed can also be measured.

The observation device according to the above-described aspect may further include: a stirring mechanism that includes a stirring shaft extending inside the culture vessel in a depth direction of the culture vessel and a stirring blade rotated about the stirring shaft and that stirs the culture fluid inside the culture vessel when the stirring blade is rotated about the stirring shaft; and a light source that is disposed outside the culture vessel and that emits illumination light toward the stirring blade, wherein the culture vessel may have, in the side surface thereof, a parallel-plate illumination window through which the illumination light emitted from the light source is transmitted; and an area, of the stirring blade, located in a light path of the illumination light may be made of a material that reflects the illumination light toward the observation window.

With this configuration, illumination light emitted from the light source and transmitted through the illumination window is reflected by the stirring blade, is then transmitted through the observation window, and enters the stereo optical system. In this case, the light source and the stereo optical system are disposed outside the culture vessel, thereby preventing the light source and the stereo optical system from obstructing the flow of the culture fluid and the cells. Furthermore, the light source and the stereo optical system can be disposed, outside the culture vessel, at positions close to each other, thus making it possible to save space.

In the observation device according to the above-described aspect, the culture vessel may have, in a bottom surface thereof, a parallel-plate observation window that is made of an optically transparent material, and the observation device may further include a light source that is disposed in an upper surface of the culture vessel and that emits illumination light toward the observation window, wherein the stereo optical system may be disposed outside the culture vessel and may image light that is transmitted from the cells through the observation window and that is emitted toward an outside of the culture vessel.

With this configuration, the flow of the culture fluid and the cells in the culture vessel is prevented from being obstructed by the stereo optical system. Furthermore, the shape of the culture vessel can be made simple.

In the observation device according to the above-described aspect, the light source may radiate the illumination light toward the observation window at an angle in a direction intersecting an arrangement direction of the viewpoints of the stereo optical system.

With this configuration, because the refractive indexes are different in the culture fluid and inside the cell, light is bent at the boundary between the culture fluid and the cell. In this case, a region corresponding to light that is bent in such a direction as to pass through the outside of the pupil becomes dark in the image plane, and a region corresponding to light that is bent in such a direction as to pass through the inside of the pupil becomes bright in the image plane, thus making it possible to acquire an image in which the contrast of the cells has been improved.

In the observation device according to the above-described aspect, the culture vessel may be a bioreactor; and the stereo image-acquisition optical system may acquire images of the cells floating in the bioreactor.

REFERENCE SIGNS LIST 1, 51, 61, 71 observation device
7 image analysis unit
9 culture vessel
9c illumination window
25 stereo optical system (stereo image-acquisition optical system)
27 image-acquisition device (stereo image-acquisition optical system)
17 stirring mechanism
17a stirring shaft
17b stirring blade
21 light source
31 objective optical system
33 aperture opening part
35 deflecting prism (prism)
37 imaging optical system
43 mirror (oblique illumination part)
63 observation window
65 transmissive window
73 culture bag (culture vessel)
S cell

The invention claimed is:

1. An observation device comprising:
a stereo image-acquisition optical system that acquires images of cells floating in a culture fluid inside a culture vessel; and
an analyzer that calculates a cell density of the cells on the basis of the images acquired by the stereo image-acquisition optical system,
wherein the analyzer identifies a three-dimensional position of each of the cells included in the images and calculates the cell density on the basis of the number of cells present within a predetermined three-dimensional region,
wherein the stereo image-acquisition optical system comprises:
a stereo optical system that forms, for the same cell floating in the culture fluid, two views with parallax due to being viewed from different viewpoints; and
an imager that acquires images of the two views formed by the stereo optical system,
wherein the stereo optical system comprises:
an objective optical system that comprises lenses and that focuses light from the cells; and
an aperture opening that splits the light focused by the objective optical system,
wherein the aperture opening includes a first opening and a second opening, and
wherein the imager acquires images of light that passes through the first opening and the second opening respectively as the images of the two views, the images of the two views being acquired from the same observation position at the same time.

2. The observation device according to claim 1, wherein the stereo optical system further comprises a prism that deflects light rays obtained after the splitting at the aperture opening.

3. The observation device according to claim 1, wherein the stereo optical system further comprises an imaging optical system that comprises lenses and that separately images light rays obtained after the splitting at the aperture opening.

4. The observation device according to claim 1, wherein the stereo optical system comprises a prism that focuses light from the cells, thereby splitting the light into the two views.

5. The observation device according to claim 1, further comprising a mirror that radiates illumination light onto the cells at an angle in a direction intersecting an arrangement direction of the viewpoints of the stereo optical system.

6. The observation device according to claim 1, wherein the culture vessel has, in a side surface thereof, a parallel-plate observation window that is made of an optically transparent material, and
the stereo optical system is disposed outside the culture vessel and images light that is transmitted from the cells through the observation window and is emitted toward an outside of the culture vessel.

7. The observation device according to claim 1, wherein the culture vessel has, in a side surface thereof, a prism that deflects light from the cells to emit the light toward an outside of the culture vessel, and
the stereo optical system is disposed outside the culture vessel and images the light emitted by the prism toward the outside of the culture vessel.

8. The observation device according to claim 1, further comprising a stirring mechanism that includes a hollow stirring shaft extending inside the culture vessel in a depth direction of the culture vessel and a stirring blade rotated about the stirring shaft and that stirs the culture fluid when the stirring blade is rotated about the stirring shaft,
wherein the stirring shaft has a parallel-plate observation window that is made of an optically transparent material; and
the stereo optical system is accommodated inside the stirring shaft and images light from the cells that is transmitted through the observation window and that enters the stirring shaft.

9. The observation device according to claim 8, further comprising a light source that emits illumination light toward the observation window from a radially outer side of the stirring shaft,
wherein the stereo optical system is not rotated about the stirring shaft.

10. The observation device according to claim 8, further comprising a light source that emits illumination light toward the observation window from a radially outer side of the stirring shaft,
wherein the stereo optical system is rotated about the stirring shaft together with the stirring shaft.

11. The observation device according to claim 6, further comprising:
a stirring mechanism that includes a hollow stirring shaft extending inside the culture vessel in a depth direction of the culture vessel and a stirring blade rotated about the stirring shaft and that stirs the culture fluid when the stirring blade is rotated about the stirring shaft; and
a light source that is accommodated inside the stirring shaft and that emits illumination light radially outward from an entire circumference of the stirring shaft while being rotated together with the stirring shaft,
wherein the stirring shaft has a ring-shaped transmissive window that is made of an optically transparent material and that surrounds the light source.

12. The observation device according to claim 6, further comprising:
a stirring mechanism that includes a hollow stirring shaft extending inside the culture vessel in a depth direction of the culture vessel and a stirring blade rotated about the stirring shaft and that stirs the culture fluid when the stirring blade is rotated about the stirring shaft; and
a light source that is accommodated inside the stirring shaft of the stirring mechanism and that emits illumination light toward the observation window,
wherein the stirring shaft has a ring-shaped transmissive window that is made of an optically transparent material and that surrounds the light source; and
the light source is not rotated about the stirring shaft.

13. The observation device according to claim 6, further comprising:
a stirring mechanism that includes a stirring shaft extending inside the culture vessel in a depth direction of the culture vessel and a stirring blade rotated about the stirring shaft and that stirs the culture fluid when the stirring blade is rotated about the stirring shaft; and
a light source that is disposed outside the culture vessel so as to be opposed to the observation window at a position shifted in a radial direction of the stirring shaft, with the stirring mechanism sandwiched therebetween, and that emits illumination light toward the observation window,
wherein the culture vessel has, in the side surface thereof, a parallel-plate illumination window through which the illumination light emitted from the light source is transmitted; and
the illumination light emitted from the light source passes through a position shifted in a longitudinal direction of the stirring shaft with respect to the stirring blade and enters the observation window.

14. The observation device according to claim 1,
wherein the culture vessel has, in a bottom surface thereof, a parallel-plate observation window that is made of an optically transparent material, and
the observation device further comprises a light source that is disposed in an upper surface of the culture vessel and that emits illumination light toward the observation window,
wherein the stereo optical system is disposed outside the culture vessel and images light that is transmitted from the cells through the observation window and that is emitted toward an outside of the culture vessel.

15. The observation device according to claim 9, wherein the light source radiates the illumination light toward the observation window at an angle in a direction intersecting an arrangement direction of the viewpoints of the stereo optical system.

16. The observation device according to claim 1,
wherein the culture vessel is a bioreactor; and
the stereo image-acquisition optical system acquires images of the cells floating in the bioreactor.

17. The observation device according to claim 1,
wherein the culture vessel is a culture bag; and
the stereo image-acquisition optical system acquires images of the cells floating in the culture bag.

18. A cell observation method comprising:
acquiring images of cells floating in a culture fluid inside a culture vessel as images of two views by using a stereo optical system including an aperture opening having two openings, the images of the two views being acquired from the same observation position at the same time;
identifying a three-dimensional position of each of the cells included in the acquired images;
calculating the number of cells present within a predetermined three-dimensional region, and
calculating a cell density on the basis of the number of cells present within the predetermined three-dimensional region and a volume of the predetermined three-dimensional region.

* * * * *